(12) United States Patent
Tan et al.

(10) Patent No.: US 9,881,312 B2
(45) Date of Patent: Jan. 30, 2018

(54) RADIO COMMUNICATION SYSTEMS AND RADIO COMMUNICATION METHODS

(71) Applicant: RAZER (ASIA-PACIFIC) PTE. LTD., Singapore (SG)

(72) Inventors: Min-Liang Tan, Singapore (SG); Sze Wei Joel Hong, Singapore (SG); Chee Oei Chan, Singapore (SG); Kah Yong Lee, Singapore (SG)

(73) Assignee: RAZER (ASIA-PACIFIC) PTE. LTD., Singapore (SG)

( * ) Notice: Subject to any disclaimer, the term of this patent is extended or adjusted under 35 U.S.C. 154(b) by 0 days.

(21) Appl. No.: 14/650,008

(22) PCT Filed: Jun. 9, 2014

(86) PCT No.: PCT/SG2014/000267
§ 371 (c)(1),
(2) Date: Jun. 5, 2015

(87) PCT Pub. No.: WO2015/190992
PCT Pub. Date: Dec. 17, 2015

(65) Prior Publication Data
US 2016/0335651 A1    Nov. 17, 2016

(51) Int. Cl.
*G06Q 30/02* (2012.01)
*A61B 5/00* (2006.01)
(Continued)

(52) U.S. Cl.
CPC ....... *G06Q 30/0207* (2013.01); *A61B 5/0002* (2013.01); *A61B 5/72* (2013.01);
(Continued)

(58) Field of Classification Search
CPC .......... G06Q 10/00; G06Q 30/00; G06F 9/54; G06F 9/50; G06F 3/033; G09G 5/00;
(Continued)

(56) References Cited

U.S. PATENT DOCUMENTS 5,440,559 A    8/1995    Gaskill
8,257,177 B1   9/2012    Saund et al.
(Continued)

FOREIGN PATENT DOCUMENTS

EP    2733608 A2    5/2014
JP    2009147761 A  7/2009
(Continued)

OTHER PUBLICATIONS

Kanis, M., Winters, N., Agamanolis, S., Gavin, A. And Cullinan, C., Apr. 2005. Toward wearable social networking with iBand. In CHI'05 extended abstracts on Human factors in computing systems (pp. 1521-1524). ACM.*
(Continued)

*Primary Examiner* — Yuwen Pan
*Assistant Examiner* — Zhitong Chen
(74) *Attorney, Agent, or Firm* — Polsinelli PC

(57) ABSTRACT

According to various embodiments, a radio communication system may be provided. The radio communication system may include: a portable device; a beacon receiving device; and a server. The portable device may include: a transmitter configured to repeatedly transmit signals; and a receiver configured to receive data from the server. The beacon receiving device may include: a receiver configured to receive signals from the portable device; and a transmitter configured to transmit an indication to the server based on the received signal. The server may include: a receiver configured to receive the indication from the beacon receiving device; and a transmitter configured to transmit data to the portable device based on the indication.

18 Claims, 10 Drawing Sheets

(51) Int. Cl.
*H04L 29/08* (2006.01)
*H04W 4/00* (2009.01)
*G09G 5/00* (2006.01)
*H04W 4/04* (2009.01)
*H04W 4/02* (2009.01)

(52) U.S. Cl.
CPC .............. *G09G 5/00* (2013.01); *H04L 67/141* (2013.01); *H04W 4/006* (2013.01); *H04W 4/008* (2013.01); *H04W 4/02* (2013.01); *H04W 4/04* (2013.01)

(58) Field of Classification Search
CPC .. G01C 21/00; A61B 5/02; A61B 5/03; A61B 5/024; A61B 5/0285; H04W 4/008; H04W 40/244; H04W 88/16; H04L 12/28; H04L 1/28
See application file for complete search history.

(56) References Cited

U.S. PATENT DOCUMENTS

| | | | | |
|---|---|---|---|---|
| 2008/0004888 | A1* | 1/2008 | Davis | G06Q 20/3224 705/26.1 |
| 2009/0031258 | A1* | 1/2009 | Arrasvuori | G06F 3/017 715/863 |
| 2009/0156272 | A1 | 6/2009 | Ohuchi et al. | |
| 2010/0197280 | A1 | 8/2010 | Hans et al. | |
| 2010/0241496 | A1 | 9/2010 | Gupta et al. | |
| 2012/0310395 | A1 | 12/2012 | El-Hoiydi | |
| 2013/0072114 | A1 | 3/2013 | Abhyanker | |
| 2013/0272554 | A1 | 10/2013 | Sommer et al. | |
| 2013/0281169 | A1 | 10/2013 | Coverstone et al. | |
| 2014/0019246 | A1 | 1/2014 | Fraccaroli | |
| 2014/0089514 | A1 | 3/2014 | Messenger et al. | |
| 2015/0009096 | A1* | 1/2015 | Lee | G06F 1/163 345/2.2 |
| 2015/0373482 | A1* | 12/2015 | Barnard | H05B 37/0272 370/338 |

FOREIGN PATENT DOCUMENTS

| | | |
|---|---|---|
| KR | 10 2013 0016835 A | 2/2013 |
| KR | 10 2013 0084993 | 7/2013 |
| WO | 2011/111952 A1 | 9/2011 |
| WO | 2013/056143 A1 | 4/2013 |

OTHER PUBLICATIONS

Kanis, M., etc. iBand a wearable device for handshake-augmented interpersonal information exchange, Feb. 23, 2014.*
Kanis et al., iBand—a wearable device for handshake-augmented interpersonal information exchange., Media Lab Europe, Human Connectedness Research Group, http://web.media.mit.edu/~stefan/hc/projects/iband/.
Kanis et al., iBand, http://web.media.mit.edu/~stefan/hc/iband/.
Written Opinion of the International Searching Authority dated Feb. 26, 2015 in the International Application No. PCT/SG2014/000267.
Extended European Search Report dated Jan. 18, 2017 in corresponding European Patent Application No. 14866790.0, 8 pages.

* cited by examiner

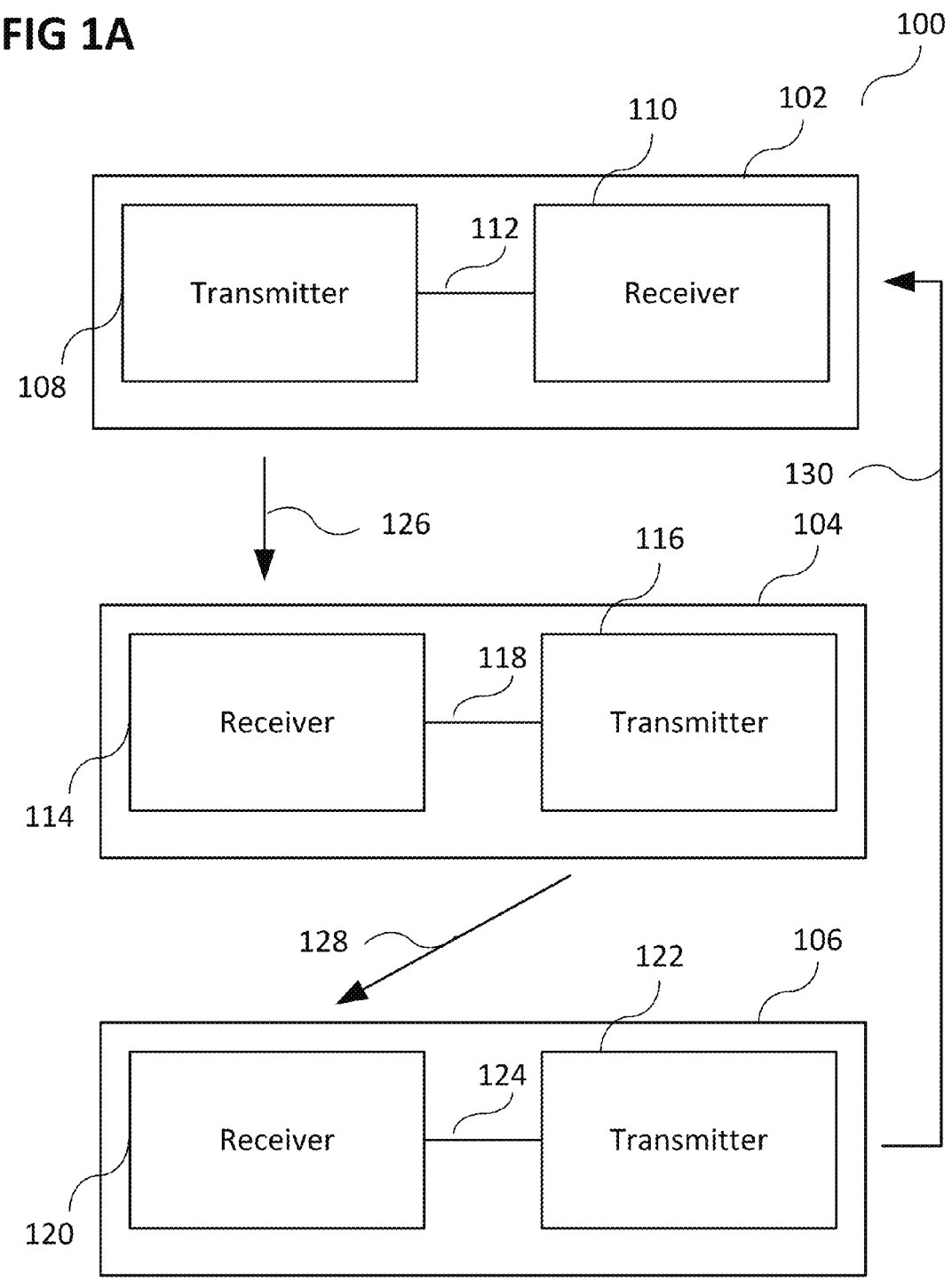

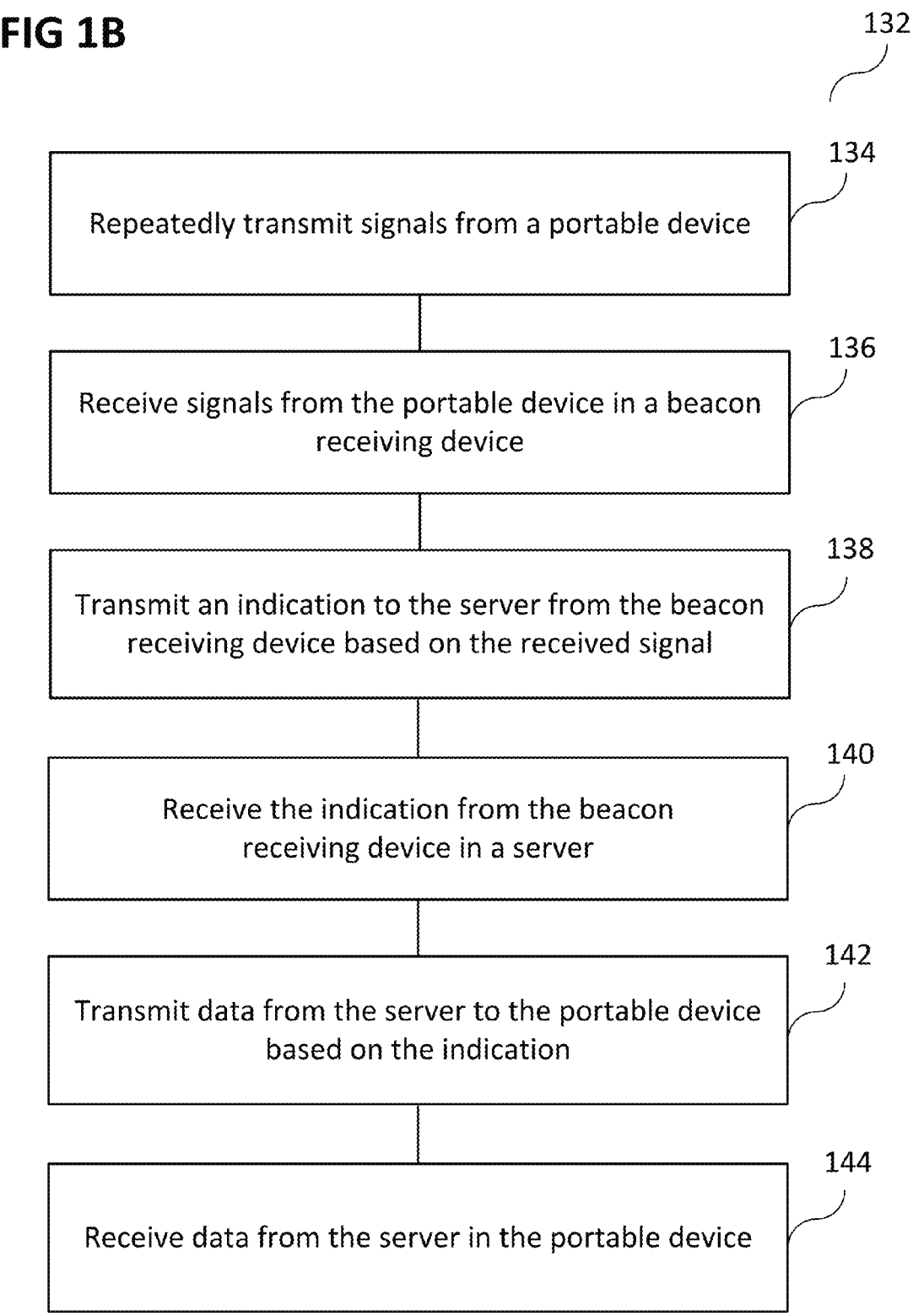

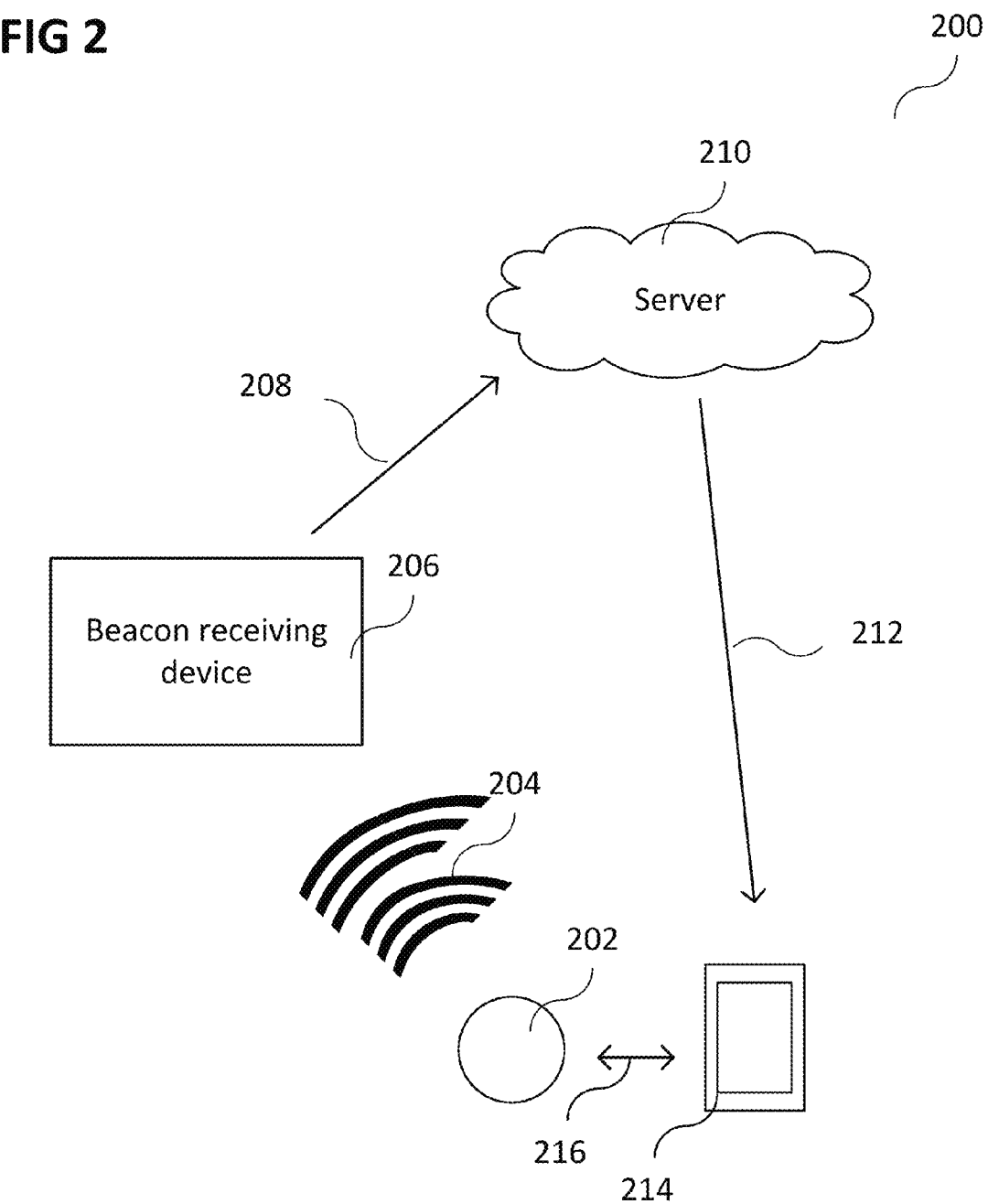

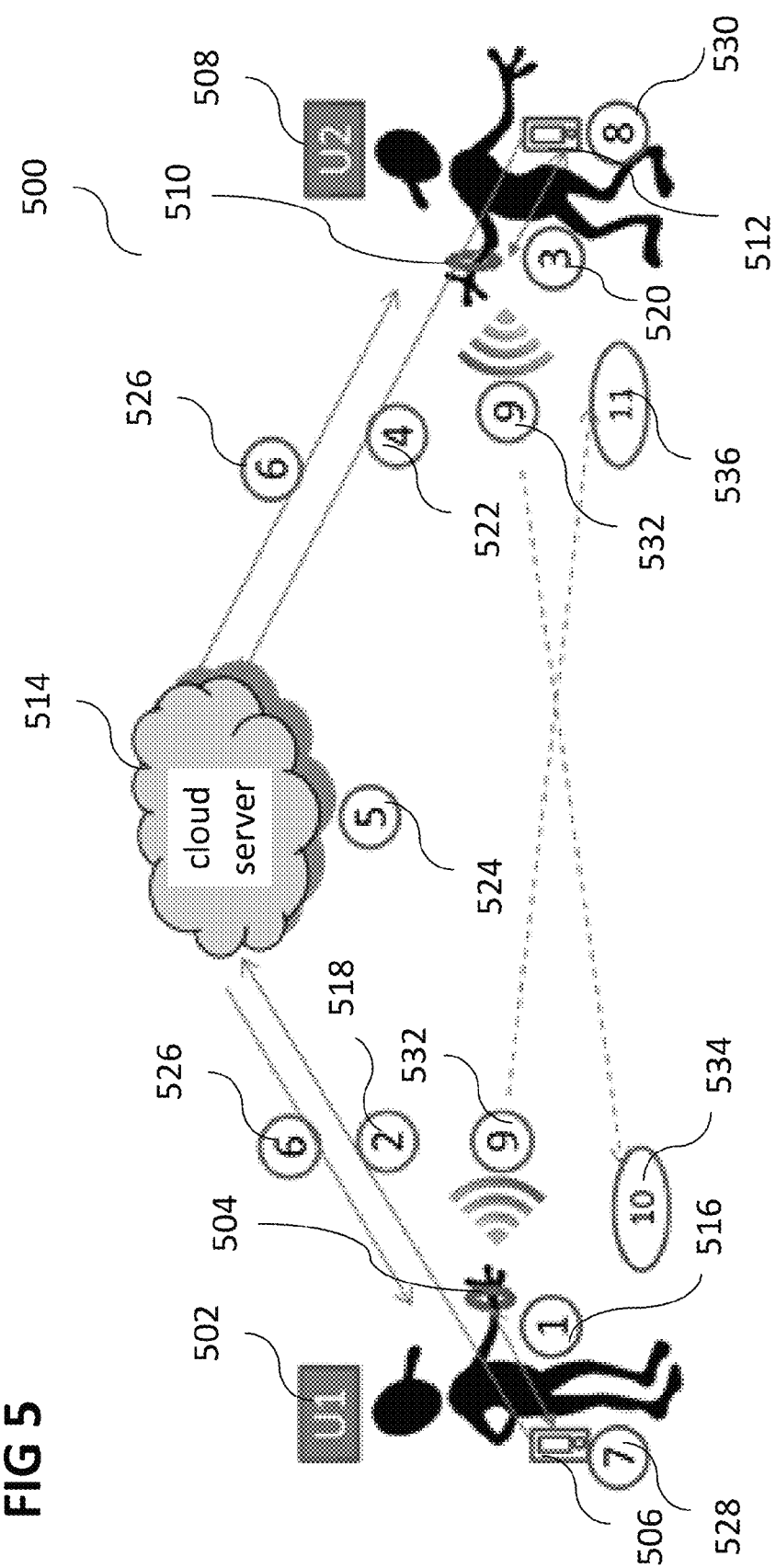

RADIO COMMUNICATION SYSTEMS AND RADIO COMMUNICATION METHODS

CROSS-REFERENCE TO RELATED APPLICATIONS

This application is a national stage entry of PCT/SG2014/000267 filed Jun. 9, 2014, said application is expressly incorporated herein in its entirety.

TECHNICAL FIELD

Various embodiments generally relate to radio communication systems and radio communication methods.

BACKGROUND

Various applications may desire transmitting data to a portable device based on the location of the portable device. Such, it may be desired to provide an efficient method for transmitting data to a portable device based on the location of the portable device.

SUMMARY OF THE INVENTION

According to various embodiments, a radio communication system may be provided. The radio communication system may include: a portable device; a beacon receiving device; and a server. The portable device may include: a transmitter configured to repeatedly transmit signals; and a receiver configured to receive data from the server. The beacon receiving device may include: a receiver configured to receive signals from the portable device; and a transmitter configured to transmit an indication to the server based on the received signal. The server may include: a receiver configured to receive the indication from the beacon receiving device; and a transmitter configured to transmit data to the portable device based on the indication.

According to various embodiments, a radio communication method may be provided. The radio communication method may include: repeatedly transmitting signals from a portable device; receiving signals from the portable device in a beacon receiving device; transmitting an indication to the server from the beacon receiving device based on the received signal; receiving the indication from the beacon receiving device in a server; transmitting data from the server to the portable device based on the indication; and receiving data from the server in the portable device.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. The dimensions of the various features or elements may be arbitrarily expanded or reduced for clarity. In the following description, various embodiments of the invention are described with reference to the following drawings, in which:

FIG. 1A shows a radio communication system according to various embodiments;

FIG. 1B shows a flow diagram illustrating a radio communication method according to various embodiments;

FIG. 2 shows a radio communication system according to various embodiments;

FIG. 5, FIG. 6, and FIG. 7 show illustrations indirect information exchange and of methods for band to band information exchange according to various embodiments.

DETAILED DESCRIPTION

Figure 3A:
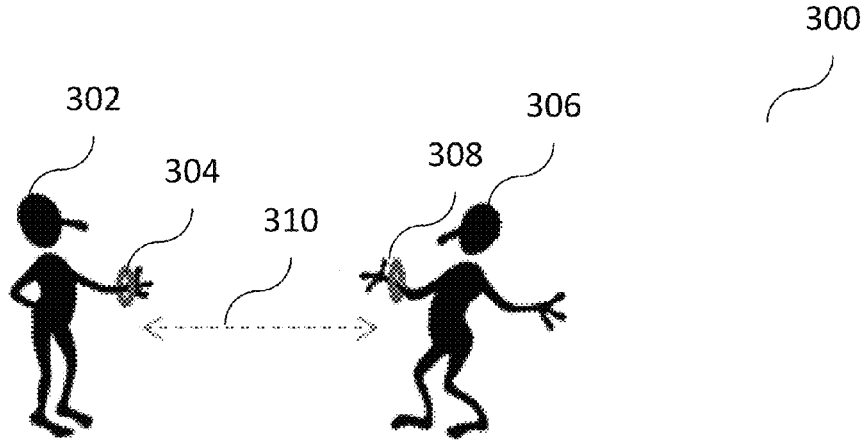
FIG. 3A shows a diagram illustrating a conventional communication method.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In order that the invention may be readily understood and put into practical effect, particular embodiments will now be described by way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

The term "coupled" (or "connected") herein may be understood as electrically coupled or as mechanically coupled, for example attached or fixed or attached, or just in contact without any fixation, and it will be understood that both direct coupling or indirect coupling (in other words: coupling without direct contact) may be provided.

In this context, the portable device as described in this description may include a memory which is for example used in the processing carried out in the portable device. In this context, the beacon receiving device as described in this description may include a memory which is for example used in the processing carried out in the beacon receiving device. In this context, the server as described in this description may include a memory which is for example used in the processing carried out in the server. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

It will be understood that band and wristband may be used interchangeable, and may for example include closed bands or bands which may be opened, for example by a mechanism identical or similar to mechanisms used for watches.

Various applications may desire transmitting data to a portable device based on the location of the portable device. According to various embodiments, systems, devices, and methods may be provided for transmitting data to a portable device based on the location of the portable device.

According to various embodiments, systems and devices for location based coupons may be provided.

FIG. 1A shows a radio communication system 100 according to various embodiments. The radio communication system may include a portable device 102, a beacon receiving device 104, and a server 106. The portable device 102 may include: a transmitter 108 configured to repeatedly transmit signals; and a receiver 110 configured to receive data from the server. The transmitter 108 of the portable device 102 and the receiver 110 of the portable device 102 may be coupled with each other, like indicated by line 112, for example electrically coupled, for example using a line or a cable, and/or mechanically coupled. The beacon receiving device 104 may include: a receiver 114 configured to receive signals from the portable device 102 (for example like illustrated by arrow 126); and a transmitter 116 configured to transmit an indication to the server 106 (for example like illustrated by arrow 128) based on the received signal. The receiver 114 of the beacon receiving device 104 and the transmitter 116 of the beacon receiving device 104 may be coupled with each other, like indicated by line 118, for example electrically coupled, for example using a line or a cable, and/or mechanically coupled. The server 106 may include: a receiver 120 configured to receive the indication from the beacon receiving device 104; and a transmitter 122 configured to transmit data to the portable device 102 (for example like illustrated by arrow 130) based on the indication. The receiver 120 of the server 106 and the transmitter 122 of the server 106 may be coupled with each other, like indicated by line 124, for example electrically coupled, for example using a line or a cable, and/or mechanically coupled.

In other words, according to various embodiments, a portable device may repeatedly send out signals based on which a beacon receiving device may determine the presence of the portable device in the vicinity of the beacon receiving device. The beacon receiving device, once determined the presence of the portable device, may inform a server about the presence, and the server may transmit data to the portable device. For example, the beacon receiving device may be provided at a fixed location.

According to various embodiments, the portable device 102 may be or may include or may be included in a mobile radio communication device.

According to various embodiments, the portable device 102 may include a mobile radio communication device (for example a mobile phone or a table computer) and a wearable device (for example a wristband).

According to various embodiments, the transmitter 108 of the portable device 102 may be provided in the wearable device.

According to various embodiments, the receiver 110 of the portable device 102 may be provided in the mobile radio communication device.

According to various embodiments, the indication may include or may be an identifier of the beacon receiving device 104.

According to various embodiments, the data may include or may be a coupon for a promotion at a location of the beacon receiving device. For example, the coupon may be an image or a code which may entitle the holder of the coupon to a reduced price of a good or a service, or even a free good or service.

According to various embodiments, the server 106 may further include a location tracking circuit configured to track a location of the portable device 102 based on the indication.

According to various embodiments, the server 106 may further include a determination circuit configured to determine whether a further portable device moves jointly with the portable device based on the tracked location information.

According to various embodiments, the data may include or may be a coupon for a joint promotion for the user of the portable device 102 and the user of the further portable device if the determination circuit (of the server 106) determines that the further portable device moves jointly with the portable device 102.

According to various embodiments, the transmitter 122 of the server 106 may further be configured to transmit the data to the further portable device if the determination circuit (of the server 106) determines that the further portable device moves jointly with the portable device 102.

According to various embodiments, the beacon receiving device 104 may include a motion determination circuit configured to determine whether a motion of the portable device 102 includes (or is) a pre-determined motion (for example a shaking motion, for example a handshake motion).

According to various embodiments, the portable device 102 may include a motion determination circuit configured to determine whether a motion of the portable device includes (or is) the pre-determined motion. The transmitter 108 of the portable device 102 may further be configured to transmit a motion identifier to the beacon receiving device 104 if the motion determination circuit of the portable device 102 determines that the motion of the portable device 102 includes (or is) the pre-determined motion. The motion determination circuit of the beacon receiving device 104 may be configured to determine whether the motion of the portable device includes (or is) the pre-determined motion based on the motion identifier. The indication may include an identifier of the beacon receiving device 104, an identifier of the portable device 102 and an identifier of the pre-determined motion if the motion determination circuit of the beacon receiving device 104 determines that the motion of the portable device 102 includes (or is) the pre-determined motion.

According to various embodiments, the server 106 may include a determination circuit configured to determine whether at least two portable devices perform the pre-determined motion at the same location at the same time.

According to various embodiments, the server 106 may further include a social network circuit configured to link users of the at least two portable devices on a social network if the determination circuit of the server 106 determines that at least two portable devices perform the pre-determined motion at the same location at the same time.

FIG. 1B shows a flow diagram 132 illustrating a radio communication method according to various embodiments. In 134, signals may be repeatedly transmitted from a portable device. In 136, signals from the portable device may be received in a beacon receiving device. In 138, an indication may be transmitted to the server from the beacon receiving device based on the received signal. In 140, the indication may be received from the beacon receiving device in a server. In 142, data may be transmitted from the server to the portable device based on the indication. In 144, data may be received from the server in the portable device.

According to various embodiments, the portable device may include or may be or may be included a mobile radio communication device.

According to various embodiments, the portable device may include a mobile radio communication device and a wearable device.

According to various embodiments, the repeatedly transmitting of signals from the portable device may be performed by the wearable device.

According to various embodiments, the receiving of data from the server in the portable device may be performed by the mobile radio communication device.

According to various embodiments, the indication may include or may be an identifier of the beacon receiving device.

According to various embodiments, the data may include or may be a coupon for a promotion at a location of the beacon receiving device.

According to various embodiments, the method may further include tracking in the server a location of the portable device based on the indication.

According to various embodiments, the method may further include determining in the server whether a further portable device moves jointly with the portable device based on the tracked location information.

According to various embodiments, the data may include or may be a coupon for a joint promotion for the user of the portable device and the user of the further portable device if the server determines that the further portable device moves jointly with the portable device.

According to various embodiments, the method may further include transmitting the data from the server to the further portable device if it is determined that the further portable device moves jointly with the portable device.

According to various embodiments, the method may further include determining in the beacon receiving device whether a motion of the portable device includes (or is) a pre-determined motion.

According to various embodiments, the method may further include: determining in the portable device whether a motion of the portable device includes (or is) the pre-determined motion; and transmitting a motion identifier from the portable device to the beacon receiving device if the portable device determines that the motion of the portable device includes (or is) the pre-determined motion. The beacon receiving device may determine whether the motion of the portable device includes (or is) the pre-determined motion based on the motion identifier. The indication may include an identifier of the beacon receiving device, an identifier of the portable device and an identifier of the pre-determined motion if the beacon receiving device determines that the motion of the portable device includes (or is) the pre-determined motion.

According to various embodiments, the method may further include determining in the server whether at least two portable devices perform the pre-determined motion at the same location at the same time.

According to various embodiments, the method may further include linking users of the at least two portable devices on a social network if the server determines that at least two portable devices perform the pre-determined motion at the same location at the same time.

According to various embodiments, a computer readable medium including program instructions which when executed by a processor cause the processor to perform a radio communication method (for example like described above) may be provided.

FIG. 2 shows a radio communication system according to various embodiments. For example, a wearable device 202 may repeatedly transmit signals 204. Once the wearable device 202 arrives in a vicinity of a beacon receiving device 206, the beacon receiving device 206 may receive the signals 204, and may thus determine that the wearable device 202 is close to the beacon receiving device 206. The beacon receiving device 206 may then transmit, like indicated by arrow 208, an indication about the presence of the wearable device 202 to a server 210, and the server 210 may, upon reception of the indication, transmit data (like indicated by arrow 212) to a mobile radio communication device 214 (for example a mobile phone or a table computer) associated with the wearable device 202 (for example like indicated by arrow 216). For example the wearable device 202 and the mobile radio communication device 214 may belong to the same user, and may communicate with each other using a short range radio communication technology, such as Bluetooth, ZigBee, wireless local area network, or infrared. For example, the beacon receiving device may be provided at a fixed location, for example in a shop, and the data transmitted from the server 210 may include information about a promotion going on in the shop, for example a coupon related to the promotion.

Various embodiments generally relate to radio communication devices and methods for controlling a radio communication device.

For portable or wearable devices, the amount of energy capacity (for example in a battery) may be very limited. As such, a method of conserving energy while attempt to achieve to intended function may be desired.

According to various embodiments, a radio communication device may be provided. The radio communication device may include: a memory circuit configured to store data to be broadcasted; a communication circuit configured to establish a wireless connection with a first further radio communication device; and a transmitter configured to at least one of broadcast signals based on the stored data or transmit a signal based on the stored data to the first further radio communication device using the communication circuit; wherein the communication circuit is configured to receive information from the first further radio communication device based on a signal broadcasted by a second further radio communication device, free from the communication circuit receiving the signal from the second further radio communication device.

According to various embodiments, a method for controlling a radio communication device may be provided. The method may include: storing data to be broadcasted; establishing a wireless connection with a first further radio communication device using a communication circuit; at least one of broadcasting signals based on the stored data or transmitting a signal based on the stored data to the first further radio communication device using the communication circuit; and receiving using the communication circuit information from the first further radio communication device based on a signal broadcasted by a second further radio communication device, free from the communication circuit receiving the signal from the second further radio communication device.

In this context, the radio communication device as described in this description may include a memory which is for example used in the processing carried out in the radio communication device. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

A radio communication device may be a mobile radio communication device, like for example a mobile phone or a tablet computer, or may be a wearable device, for example a band or a wristband.

It will be understood that band and wristband may be used interchangeable, and may for example include closed bands or bands which may be opened, for example by a mechanism identical or similar to mechanisms used for watches.

Current wireless wearable devices (like for example fitness bands, watches etc.) may make use of wireless low energy communication protocol (BLE (Bluetooth low energy)) to conserve power while provide linkage to host device such as smart phone. However so far none of the wearable devices offers a device to device information exchange feature due to high energy consumption if a conventional method were to use.

For portable or wearable devices, the amount of energy capacity (for example in a battery) may be very limited. As such, a method of conserving energy while attempt to achieve to intended function may be desired.

Current wireless technology has come to a point where for a good wireless link within a 10 to 20 m range, the energy needed to transmit data may be almost the same as energy needed to scan and receive data. In some case, it is already shown that energy needed to scan and receive data is higher than energy needed to transmit data.

A typical portable communication method may be for one device to transmit a short burst at a certain interval, for example $\tau$ with period $\rho$. On the receiver end, in an ideal case, the device may also wake up at interval $\tau$ with period $\rho$ to listen for any incoming packet. In practice this may be rarely achievable since both communication devices may be operating at different clocks and in time both devices' clocking may drift from one another. In practice, the receiver may need to have a wider opening window to tailor for clock tolerances between the two devices, so that the actual period of receiver will may be $\rho \pm \mathrm{u}$ where $\mathrm{u}$ may be the addition time needed before and after the period to cater for this practical issue; for example, $\mathrm{u} = \frac{1}{2}\rho$. The task of scanning and receiving wireless data packet may become more energy consuming.

If actual wireless data communication were to take place, assuming one device is transmitter and another device act as scanner and receiver, the strain may be placed on the scanner (in other words: the receiver) as it may consume more energy. Worst still, under practical device to device communication, it may be more likely that devices need to transmit as well as to listen for data or respond. Under limited energy capacity for such portable/wearable device (for example with a typical 3V to 3.7V with 30 mAh to 300 mAh depending on size) use for such application may drain off energy within 1 to 2 days, putting aside other functions that may be desired to process in the device.

In the following, a band to band information exchange will be described.

FIG. 3A shows a diagram 300 illustrating a conventional communication method. A first user 302 may wear a first wearable device 304 (for example a first band, which may be referred to as Band-1). A second user 306 may wear a second wearable device 308 (for example a second band, which may be referred to as Band-2). The first wearable device 304 and the second wearable device 308 may communicate with each other, like illustrated by arrow 310.

The first wearable device 304 may transmit information and the second wearable device 308 may receive information from the first wearable device 304 directly. The first wearable device 304 may transmit randomly and the second wearable device 308 may stay in receive mode since there is no synchronization mechanism between the two bands. If both parties wish to transmit information to each other, both wearable devices may have to transmit randomly in periodical manner and switch to scanning mode after transmission so that they are able to receive information from the other party.

According to various embodiments, indirect communication leverage on higher energy capacity device such as a smart phone (1500-2000 mAH) to perform the scanning and receive function while relegate portable device to just serve as transmit function may be provided. This may simplify the complexity of device to device communication for the portable device and may allow the extension of operating life of the device.

Furthermore, according to various embodiments, there may be no sensitive information being stored or transmits during this transaction. The security of such info may be resided in a secured server, which may be an easier and logical way of managing sensitive information.

According to various embodiments, an indirect device to device (D2D) wireless communication method may be provided.

According to various embodiments, devices and methods may be provided for conserving energy capacity in a wearable device or radio communication device.

The conservation of energy in the wearable device can be done by leveraging on the battery power of the smartphone for part of all of the processing functions of the wearable device.

Various devices and methods may be provided for the wearable device to leverage on the battery power of the smartphone. According to various embodiments, the wearable device may transmit periodically to scan for other devices ("Scanning") and to link with the smartphone for further processing such as transmitting and receiving information ("beaconing") from other smartphones or server. According to various embodiments, the wearable device may link with the smartphone to do both the scanning and beaconing functions of the wearable device. So although the wearable device and the smartphone may be linked via BLE (Bluetooth Low Energy), to save more than half of the energy of the wearable device taken up by scanning and beaconing functions, these functions may be done by the smartphone on the wearable device's behalf.

Figure 3D:
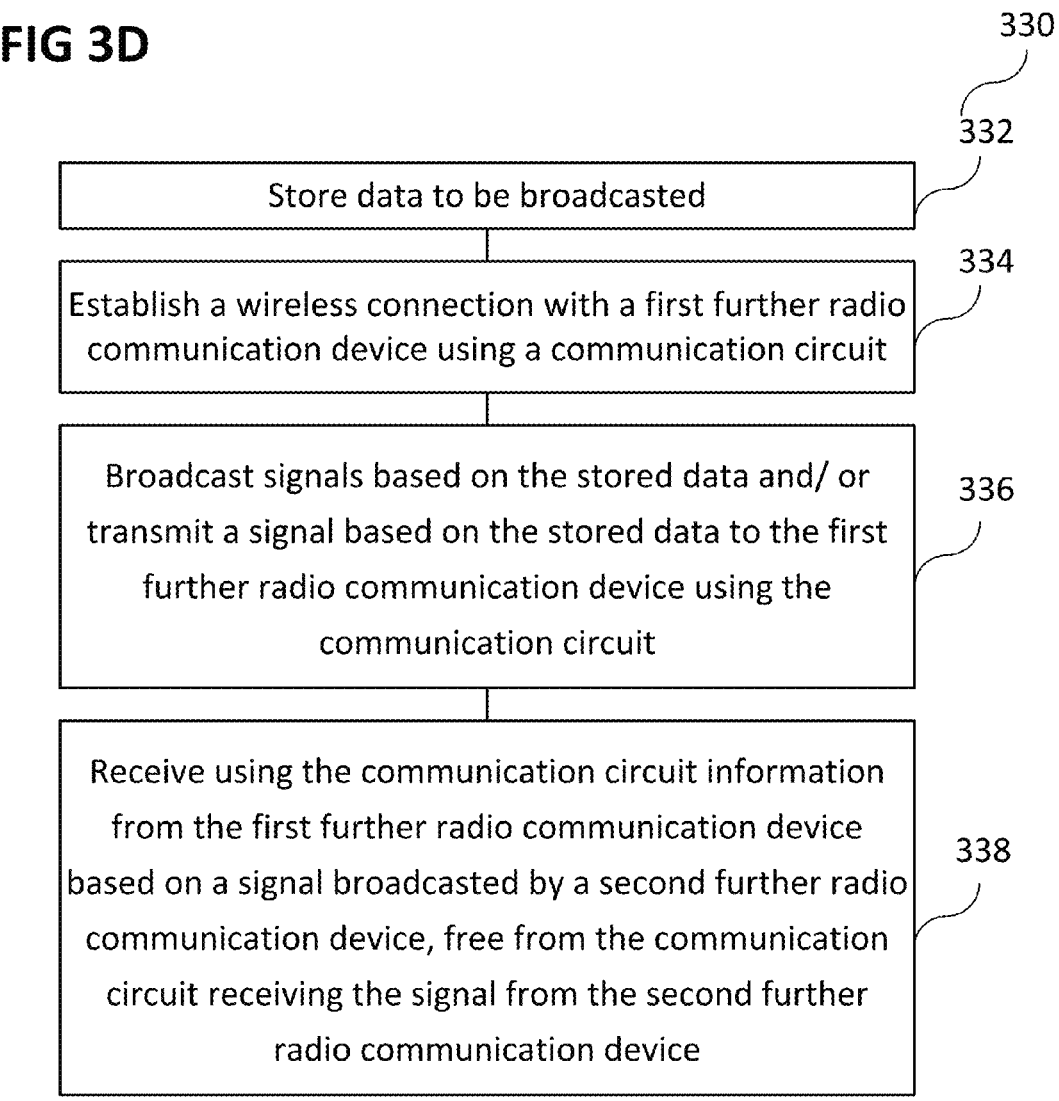
FIG. 3D shows a flow diagram illustrating a method for controlling a radio communication device.
Figure 3B:
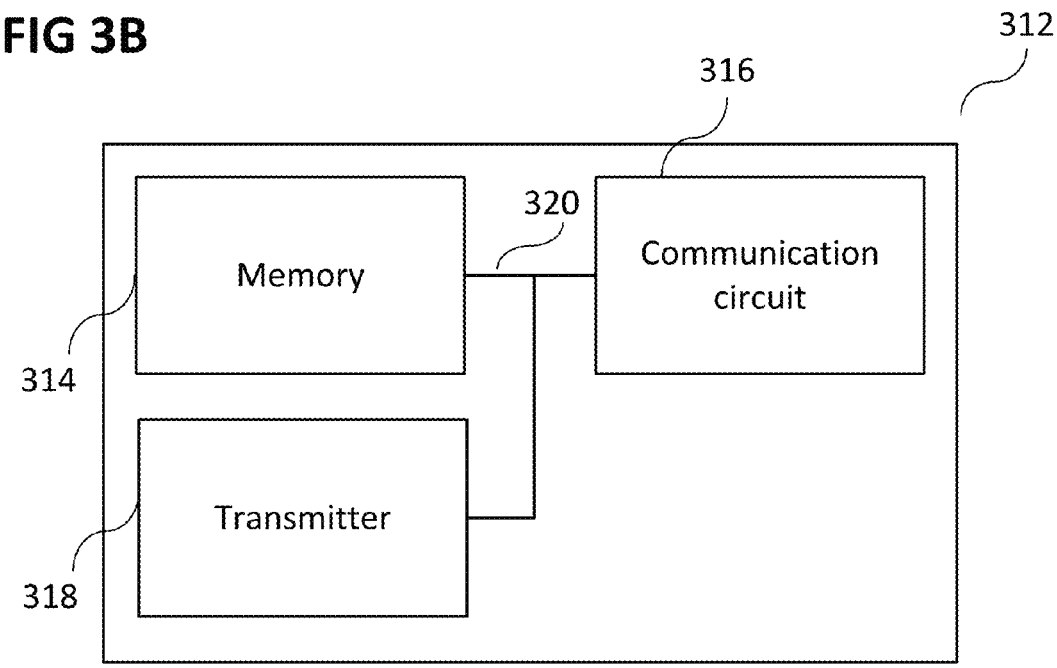
FIGS. 3B and 3C show radio communication devices according to various embodiments.

FIG. 3B shows a radio communication device 312 according to various embodiments. The radio communication device 312 may include a memory circuit 314 configured to (for example permanently) store data to be broadcasted. The radio communication device 312 may further include a communication circuit 316 configured to establish a wireless connection with a first further radio communication device (not shown in FIG. 3B). The radio communication device 312 may further include a transmitter 318 configured to at least one of broadcast signals based on the stored data or transmit a signal based on the stored data to the first further radio communication device using the communication circuit 316. The communication circuit 316 may be configured to receive information from the first further radio communication device based on a signal broadcasted by a second further radio communication device (not shown in FIG. 3B), free from (in other words: without) the communication circuit 316 receiving the signal from the second further radio communication device. The memory circuit 314 (in other words: memory), the communication circuit 316, and the transmitter 318 may be coupled with each other, like indicated by lines 320, for example electrically coupled, for example using a line or a cable, and/or mechanically coupled.

In other words, a radio communication device 312 may connect with a first further radio communication device, and may either broadcast signals or instruct the first further radio communication device to broadcast signals on behalf of the radio communication device 312, and may, via the first further radio communication device, receive information based on signals broadcasted by a second further radio communication device.

According to various embodiments, the radio communication device 312 may be an ultra low power device.

While there may be various definitions of ULP (ultra low power), it may be helpful to consider it in the context of batteries because they are easily the most common energy source for ULP designs today. Medical applications in which electronic devices are implanted in or attached to the body are good examples of ULP designs that run on batteries. Here are three examples:

Implanted medical device. Size and battery life are primary considerations. Power dissipation of 10 μW and battery life of 15,000 hours would be typical.

In-ear device. Size becomes more important that life, which indicates button cell. Typical power dissipation of 1 mW and 1,500-hour life.

Surface-of-skin device. Limiting factor is the ability of skin surface to dissipate heat. Typical power dissipation of 10 mW and 150-hour life.

To operate from a very small power supply may demand an efficient RF (radio frequency) transceiver with minimal, or "ultra-low power" (ULP) energy consumption.

According to various embodiments, the radio communication device 312 may be a wearable device.

According to various embodiments, the radio communication device 312 may be a wristband or may be wearable to a body.

Figure 3C:
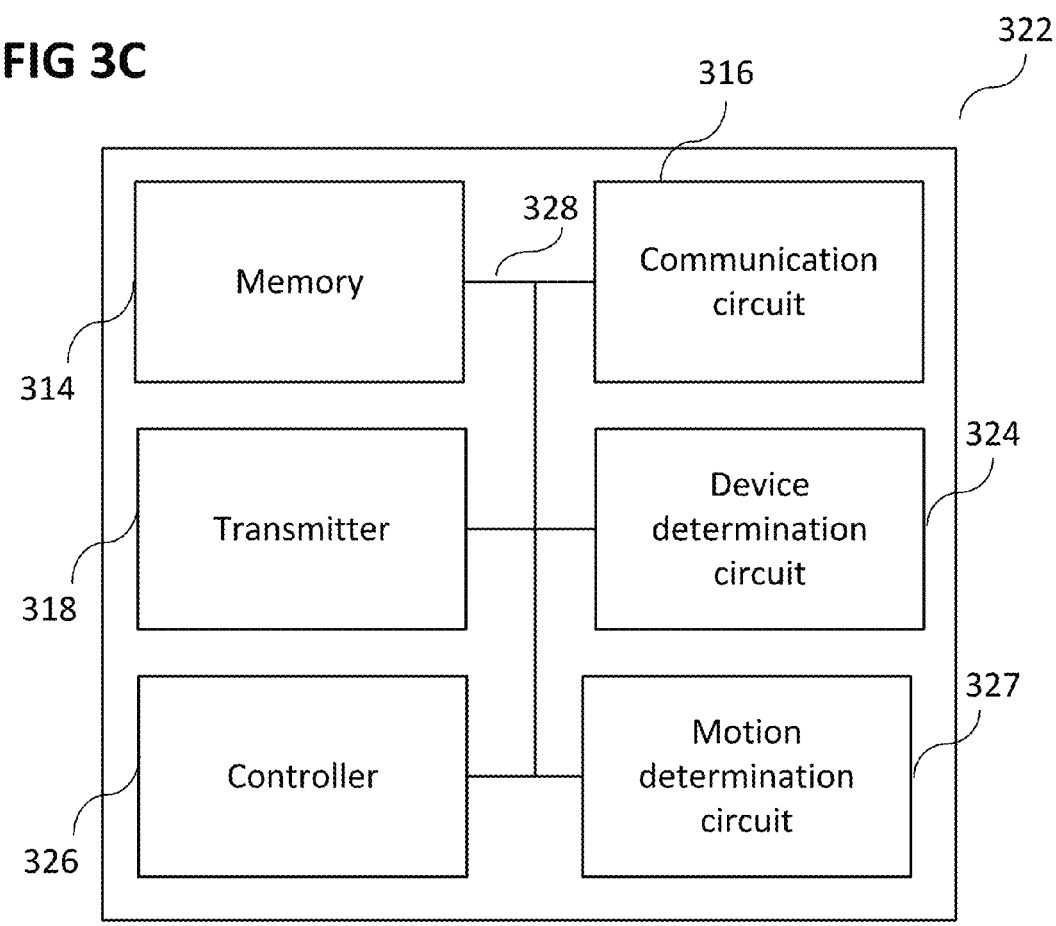

FIG. 3C shows a radio communication device 322 according to various embodiments. The radio communication device 322 may, similar to the radio communication device 312 shown in FIG. 3B, include a memory circuit 314 configured to (for example permanently) store data to be broadcasted. The radio communication device 322 may, similar to the radio communication device 312 shown in FIG. 3B, further include a communication circuit 316 configured to establish a wireless connection with a first further radio communication device (not shown in FIG. 3C). The radio communication device 322 may, similar to the radio communication device 312 shown in FIG. 3B, further include a transmitter 318 configured to at least one of broadcast signals based on the stored data or transmit a signal based on the stored data to the first further radio communication device using the communication circuit 316. The communication circuit 316 may be configured to receive information from the first further radio communication device based on a signal broadcasted by a second further radio communication device (not shown in FIG. 3C), free from (in other words: without) receiving the signal from the second further radio communication device. The radio communication device 322 may further include a device determination circuit 324, like will be described in more detail below. The radio communication device 322 may further include a controller 326, like will be described in more detail below. The radio communication device 322 may further include a motion determination circuit 327, like will be described in more detail below. The memory circuit 314 (in other words: memory), the communication circuit 316, the transmitter 318, the device determination circuit 324, the controller 326, and the motion determination circuit 327 may be coupled with each other, like indicated by lines 328, for example electrically coupled, for example using a line or a cable, and/or mechanically coupled.

According to various embodiments, the transmitter 318 may be configured to broadcast signals according to a pre-determined timing scheme, the pre-determined timing scheme including (or being) a pre-determined number of transmission in a pre-determined period of time. The device determination circuit 324 may be configured to determine whether another radio communication device is in a communication range of the radio communication device 322. The controller 326 may be configured to change the pre-determined timing scheme to increase the number of transmissions in the pre-determined period of time if the device determination circuit 324 determines that another radio communication device is in the communication range of the radio communication device 322.

According to various embodiments, the transmitter 318 may be configured to repeatedly transmit signals at a pre-determined time interval. The controller 326 may be configured to decrease the time interval if the device determination circuit 324 determines that another radio communication device is in the communication range of the radio communication device 322.

According to various embodiments, the transmitter 318 may be configured to repeatedly transmit signals with a pre-determined frequency. The controller 326 may be configured to increase the frequency if the device determination circuit 324 determines that another radio communication device is in the communication range of the radio communication device 322.

According to various embodiments, the transmitter 318 may further be configured to transmit information to another radio communication device in a communication session. The device determination circuit 324 may be configured to determine based on a location of the radio communication device 322 whether another radio communication device is in a communication range of the radio communication device 322. The controller 326 may be configured to stop the communication session if the device determination circuit 324 determines that no further radio communication device is in the communication range of the radio communication device 322.

According to various embodiments, the motion determination circuit 327 may be configured to determine whether a motion of the radio communication device comprises a pre-determined motion.

According to various embodiments, a radio communication system may be provided. The radio communication system may include the radio communication device (for example as described with reference to FIG. 3B or FIG. 3C above), and the first further radio communication device. The radio communication system according to various embodiments may for example furthermore include a server.

According to various embodiments, the radio communication device may be a wearable device. The first further radio communication device may be a mobile phone.

According to various embodiments, the mobile phone may be configured to transmit data indicating a location of the mobile phone to a server.

According to various embodiments, the mobile phone may be configured to determine whether a further radio communication device is near the mobile phone.

According to various embodiments, the mobile phone may be configured to determine whether a further radio communication device is near the mobile phone based on data received from a server.

According to various embodiments, the mobile phone may be configured to instruct the wearable device to broadcast the signals based on the stored data if the mobile phone determines that a further radio communication device is near the mobile phone.

According to various embodiments, the wearable device may be configured to transmit the signal based on the stored data to the mobile phone using the communication circuit. The mobile phone may be configured to broadcast the signals based on the signal transmitted from the wearable device if the mobile phone determines that a further radio communication device is near the mobile phone.

FIG. 3D shows a flow diagram 330 illustrating a method for controlling a radio communication device. In 332, data to be broadcasted may be stored. In 334, a wireless connection may be established with a first further radio communication device using a communication circuit. In 336 signals may be broadcasted based on the stored data and/or a signal may be transmitted based on the stored data to the first further radio communication device using the communication circuit. In 338, information from the first further radio communication device may be received using the communication circuit based on a signal broadcasted by a second further radio communication device, free from the communication circuit (directly) receiving the signal from the second further radio communication device.

According to various embodiments, the radio communication device may be an ultra low power device.

According to various embodiments, the radio communication device may be a wearable device.

According to various embodiments, the radio communication device may be a wristband or may be wearable to a body.

According to various embodiments, the method may further include: broadcasting signals according to a pre-determined timing scheme, the pre-determined timing scheme including a pre-determined number of transmission in a pre-determined period of time; determining whether another radio communication device is in a communication range of the radio communication device; and changing the pre-determined timing scheme to increase the number of transmissions in the pre-determined period of time if the device determination circuit determines that another radio communication device is in the communication range of the radio communication device.

According to various embodiments, the method may further include repeatedly transmitting signals at a pre-determined time interval; and decreasing the time interval if the device determination circuit determines that another radio communication device is in the communication range of the radio communication device.

According to various embodiments, the method may further include: repeatedly transmitting signals with a pre-determined frequency; and increasing the frequency if it is determined that another radio communication device is in the communication range of the radio communication device.

According to various embodiments, the method may further include: transmitting information to another radio communication device in a communication session; determining based on a location of the radio communication device whether another radio communication device is in a communication range of the radio communication device; and stopping the communication session if the device determination circuit determines that no further radio communication device is in the communication range of the radio communication device.

According to various embodiments, the method may further include determining whether a motion of the radio communication device comprises a pre-determined motion.

According to various embodiments, a method for controlling a radio communication system may be provided. The method may include: controlling a radio communication device according to one of the methods described above; and controlling the first further radio communication device.

According to various embodiments, the radio communication device may be a wearable device; and the first further radio communication device may be a mobile phone.

According to various embodiments, the method may further include the mobile phone transmitting data indicating a location of the mobile phone to a server.

According to various embodiments, the method may further include the mobile phone determining whether a further radio communication device is near the mobile phone.

According to various embodiments, the method may further include the mobile phone determining whether a further radio communication device is near the mobile phone based on data received from a server.

According to various embodiments, the method may further include the mobile phone instructing the wearable device to broadcast the signals based on the stored data if the mobile phone determines that a further radio communication device is near the mobile phone.

According to various embodiments, the method may further include: the wearable device transmitting the signal based on the stored data to the mobile phone using the communication circuit; and the mobile phone broadcasting the signals based on the signal transmitted from the wearable device if the mobile phone determines that a further radio communication device is near the mobile phone.

Figure 4A:
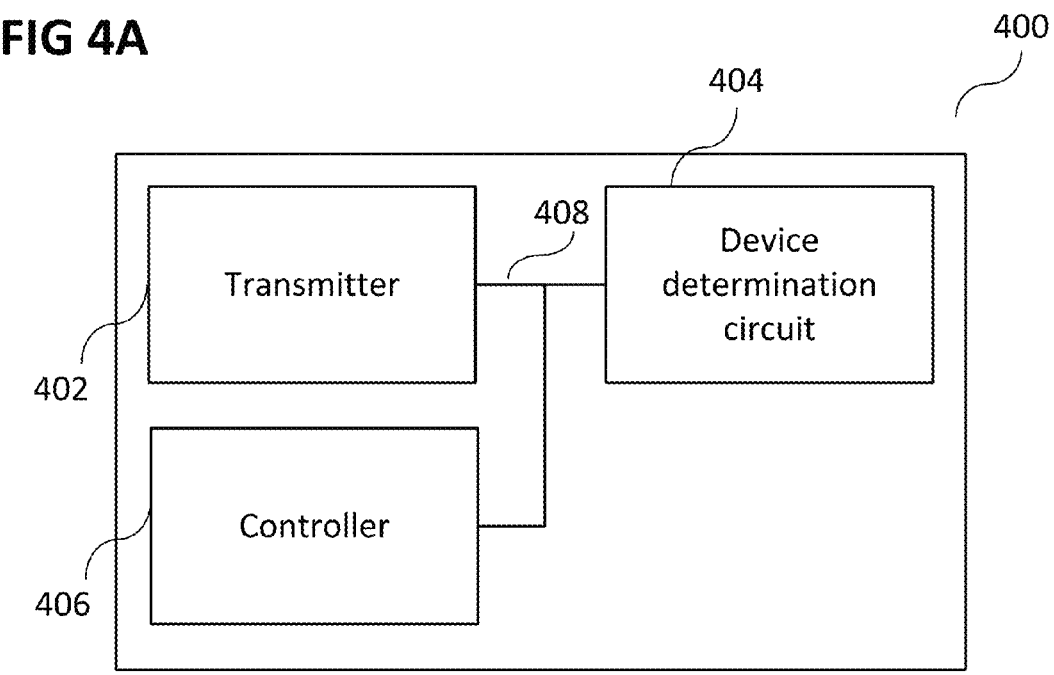
FIG. 4A shows a radio communication device according to various embodiments.

FIG. 4A shows a radio communication device 400 according to various embodiments. The radio communication device 400 may include a transmitter 402 configured to transmit signals according to a pre-determined timing scheme. The pre-determined timing scheme may include or may define a pre-determined number of transmission in a pre-determined period of time. The radio communication device 400 may further include a device determination circuit 404 configured to determine (for example based on a location of the radio communication device) whether another radio communication device is in a communication range of the radio communication device 400. The radio communication device 400 may further include a controller 406 configured to change the pre-determined timing scheme to increase the number of transmissions in the pre-determined period of time if the device determination circuit determines that another radio communication device is in the communication range of the radio communication device. The transmitter 402, the device determination circuit 404, and the controller 406 may be coupled with each other, like indicated by lines 408, for example electrically coupled, for example using a line or a cable, and/or mechanically coupled.

In other words, the radio communication device 400 may adjust how often it transmits a signal based on whether another radio communication device is near to itself.

According to various embodiments, the transmitter 402 may be configured to repeatedly transmit signals at a pre-determined time interval. The controller 406 may be configured to decrease the time interval if the device determination circuit 404 determines that another radio communication device is in the communication range of the radio communication device 400.

According to various embodiments, the transmitter 402 may be configured to repeatedly transmit signals with a pre-determined frequency. The controller 406 may be configured to increase the frequency if the device determination circuit 404 determines that another radio communication device is in the communication range of the radio communication device 400.

According to various embodiments, the radio communication device 400 may be a mobile radio communication device, for example a mobile phone or a tablet computer.

According to various embodiments, the radio communication device 400 may be a wearable device.

According to various embodiments, the device determination circuit 404 may be configured to receive from a further radio communication device information indicating whether another radio communication device is in a communication range of the radio communication device 400.

According to various embodiments, the radio communication device 400 may be a wearable device. The further radio communication device may be a mobile radio communication device, like for example a mobile phone or a tablet computer.

According to various embodiments, the device determination circuit 404 may be configured to determine whether another radio communication device is in a communication range of the radio communication device 400 based on whether a signal is received (for example in the radio communication device 400 or further radio communication device connected to the radio communication device 400) from another radio communication device.

According to various embodiments, the device determination circuit 404 may be configured to determine whether another radio communication device is in a communication range of the radio communication device 400 based on whether a signal is received (for example in the radio communication device 400 or yet a further radio communication device connected to the radio communication device 400) from a further radio communication device connected to another radio communication device.

According to various embodiments, the transmitter 402 may be configured to transmit signals based on at least one of a short range radio communication protocol, a Bluetooth communication protocol, a ZigBee communication protocol, a Wireless Local Area Network communication protocol, or an infrared communication protocol.

Figure 4B:
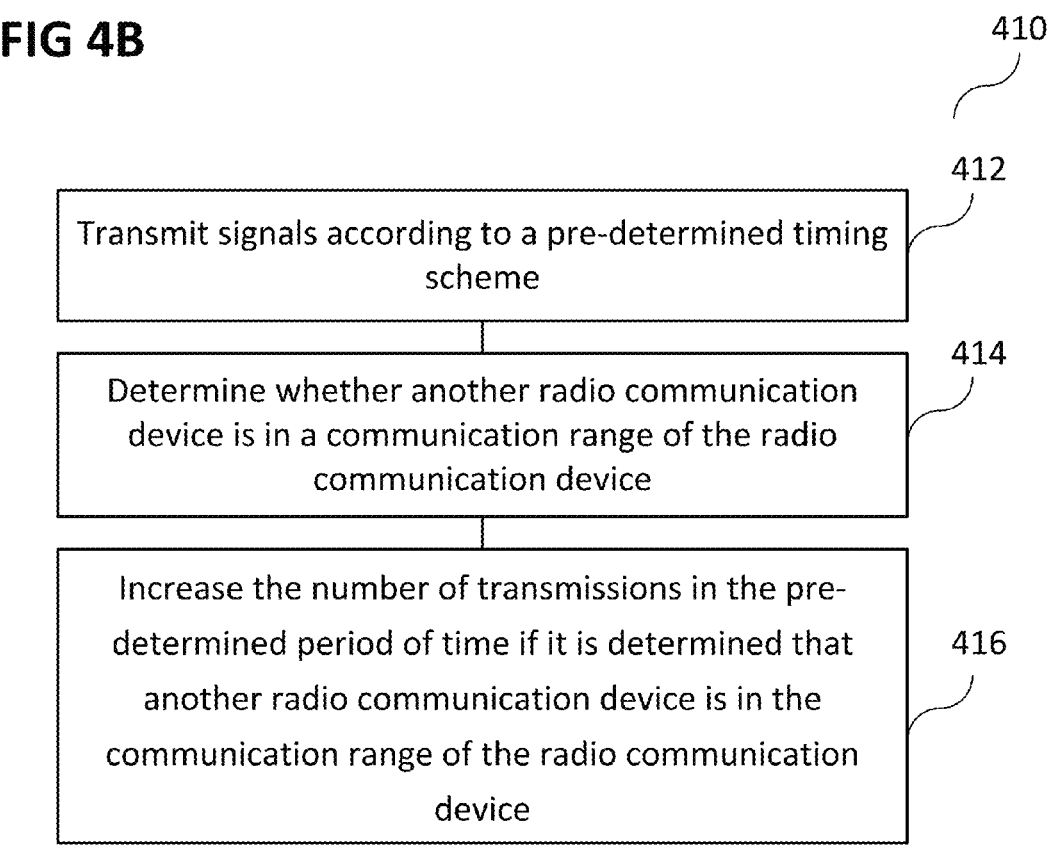
FIG. 4B shows a flow diagram illustrating a method for controlling a radio communication device.

FIG. 4B shows a flow diagram 410 illustrating a method for controlling a radio communication device. In 412, signals may be transmitted according to a pre-determined timing scheme. The pre-determined timing scheme may include or may define a pre-determined number of transmission in a pre-determined period of time. In 414, it may be determined (for example based on a location of the radio communication device) whether another radio communication device is in a communication range of the radio communication device. In 416, the number of transmissions in the pre-determined period of time may be increased if it is determined that another radio communication device is in the communication range of the radio communication device.

According to various embodiments, the method may further include: repeatedly transmitting signals at a pre-determined time interval; and decreasing the time interval if it is determined that another radio communication device is in the communication range of the radio communication device.

According to various embodiments, the method may further include: repeatedly transmitting signals with a pre-determined frequency; and increasing the frequency if it is determined that another radio communication device is in the communication range of the radio communication device.

According to various embodiments, the radio communication device may be a wearable device.

According to various embodiments, the method may further include receiving from a further radio communication device information indicating whether another radio communication device is in a communication range of the radio communication device.

According to various embodiments, the radio communication device may be a wearable device. The further radio communication device may be a mobile radio communication device.

According to various embodiments, the method may further include determining whether another radio communication device is in a communication range of the radio communication device based on whether a signal is received from another radio communication device.

According to various embodiments, the method may further include determining whether another radio communication device is in a communication range of the radio communication device based on whether a signal is received from a further radio communication device connected to another radio communication device.

According to various embodiments, the method may further include transmitting the signals based on at least one of a short range radio communication protocol, a Bluetooth communication protocol, a ZigBee communication protocol, a Wireless Local Area Network communication protocol, or an infrared communication protocol.

Figure 4C:
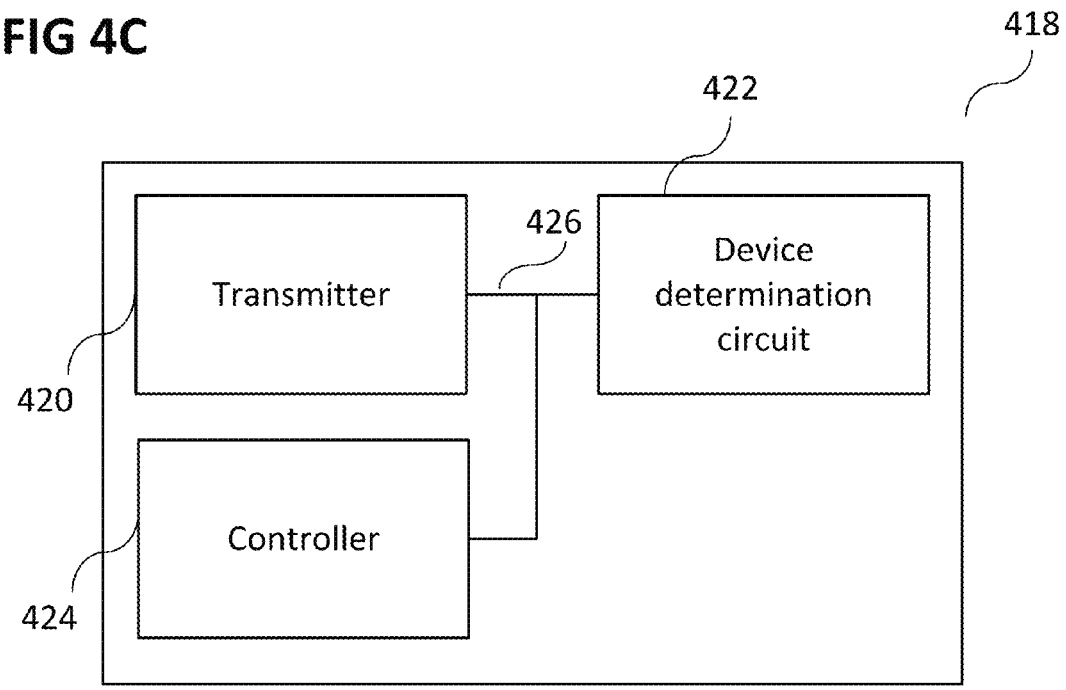
FIG. 4C shows a radio communication device according to various embodiments.

FIG. 4C shows a radio communication device 418 according to various embodiments. The radio communication device 418 may include a transmitter 420 configured to transmit information to another radio communication device in a communication session. Once it is determined that the other band is out of reach, communication is ended. Then a periodic "ping" may be started. Thus, communication may not be entirely stopped, but rather the communication presently going on is stopped, which may be expressed as stopping a "communication session". The radio communication device 418 may further include a device determination circuit 422 configured to determine based on a location of the radio communication device whether another radio communication device is in a communication range of the radio communication device. The radio communication device 418 may further include a controller 424 configured to stop the communication session if the device determination circuit 422 determines that no further radio communication device is in the communication range of the radio communication device 418. The transmitter 420, the device determination circuit 422, and the controller 424 may be coupled with each other, like indicated by lines 426, for example electrically coupled, for example using a line or a cable, and/or mechanically coupled.

In other words, the radio communication device 418 may terminate a communication session if it determines based on its location that no other radio communication device is in its vicinity.

According to various embodiments, the controller 424 may be configured to control the transmitter to repeatedly transmit signals according to a pre-determined timing scheme when the communication session is stopped. The pre-determined timing scheme may include or may define a pre-determined number of transmission in a pre-determined period of time.

According to various embodiments, the radio communication device 418 may be a mobile radio communication device, for example a mobile phone or a table computer.

According to various embodiments, the radio communication device 418 may be a wearable device.

According to various embodiments, the device determination circuit 422 may be configured to receive from a further radio communication device information indicating whether another radio communication device is in a communication range of the radio communication device 418.

According to various embodiments, the radio communication device 418 may be a wearable device. The further radio communication device may be a mobile radio communication device.

According to various embodiments, the transmitter 422 may be configured to transmit signals based on at least one of a short range radio communication protocol, a Bluetooth communication protocol, a ZigBee communication protocol, a Wireless Local Area Network communication protocol, or an infrared communication protocol.

Figure 4D:
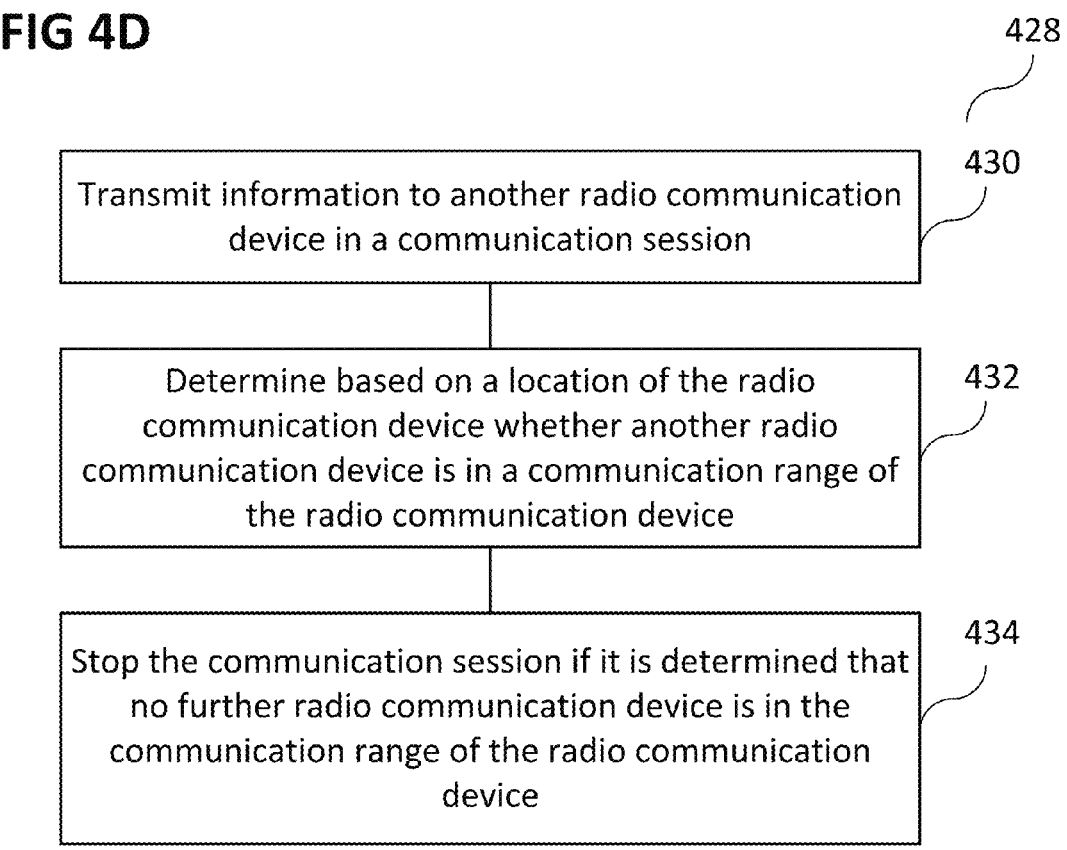
FIG. 4D shows a flow diagram illustrating a method for controlling a radio communication device.

FIG. 4D shows a flow diagram 428 illustrating a method for controlling a radio communication device. In 430, information may be transmitted to another radio communication device in a communication session. In 432, it may be determined whether another radio communication device is in a communication range of the radio communication device. In 434, the communication session may be stopped if it is determined that no further radio communication device is in the communication range of the radio communication device.

According to various embodiments, the method may further include controlling the transmitter to repeatedly transmit signals according to a pre-determined timing scheme when the communication session is stopped, the pre-determined timing scheme including a pre-determined number of transmission in a pre-determined period of time.

According to various embodiments, the radio communication device may be a wearable device.

According to various embodiments, the method may further include receiving from a further radio communication device information indicating whether another radio communication device is in a communication range of the radio communication device.

According to various embodiments, the radio communication device may be a wearable device. The further radio communication device is a mobile radio communication device.

According to various embodiments, the method may further include transmitting the signals based on at least one of a short range radio communication protocol, a Bluetooth communication protocol, a ZigBee communication protocol, a Wireless Local Area Network communication protocol, or an infrared communication protocol.

According to various embodiments, a computer readable medium may be provided including program instructions which when executed by a processor cause the processor to perform any one of the methods described above.

FIG. 5 shows an illustration 500 of an indirect information exchange and of a method for band to band information exchange according to various embodiments. A first user 502 (who may be referred to as U1) may have a first wearable device 504 (for example a first wristband) and a first mobile radio communication device 506 (for example a first mobile phone). A second user 508 (who may be referred to as U2) may have a second wearable device 510 (for example a second wristband) and a second mobile radio communication device 512 (for example a second mobile phone). A cloud server 514 may be provided.

In 516, the first user 502 (or his mobile radio communication device 506) may detect a connection between the first wearable device 504 and the first radio communication device 506 (for example a band connection to a phone). In 518, the first user 502 may update the location data (in other words: his geolocation) to the cloud server 514.

In 520, the second user 508 (or his mobile radio communication device 512) may detect a connection between the second wearable device 514 and the second radio communication device 512 (for example a band connection to a phone). In 522, the second user 522 may update the location data (in other words: his geolocation) to the cloud server 514.

In 524, the (cloud) server 514 may detect whether the first user 502 and the second user 508 are in the same vicinity based on the geolocation data. In 526, the (cloud) server 514 may inform the first user 502 and the second user 508 that there is another user in the vicinity (for example if it detects that the first user 502 and the second user 508 are in the same vicinity based on the geolocation data).

In 528, the first mobile radio communication device 506 may inform the first wearable device 504 (of the first user 502) to broadcast information. In 530, the second mobile radio communication device 512 may inform the second wearable device 510 (of the second user 508) to broadcast information. In 532, the first wearable device 504 and the second wearable device 510 may broadcast information.

In 534, the first user 502 (for example his mobile radio communication device 506) may receive information from the second wearable device 510 and may store the information in the first mobile radio communication device 506. The information received by the first user may include a USERID (user identification or User ID), where the first user may access the cloud server for more personal information that second user allowed. If the first user does not have the access right to cloud server, the user ID may not be useful for this instant. Other information such as nickname may be contained in the second user's transmission data where this can be used to display on the first user's wearable device or phone especially when the access to cloud server is not available at the point of exchange. In 536, the second user 508 (for example his mobile radio communication device 512) may receive information from the first wearable device 504 and may store the information in the second mobile radio communication device 512.

According to various embodiments, the mobile radio communication devices, for example (mobile) phones may (for example via an app or application) constantly check for band connection and the phones may constantly update its location (geolocation) data to the server. The server may inform the phone to scan for surrounding bands when it detects more than one band in the same vicinity. Upon receiving command from server, each phone may inform its respective band to broadcast band information. Phones may also listen to broadcast info from the surrounding bands. Phones may store the band information collected into its internal memory and subsequently upload the information to the server.

Power consumption of the band may be minimized according to various embodiments with the implementation of this scheme. The band may only turn on when surrounding bands are detected. The band may only turn on for a short period of time to broadcast information. The interval of each broadcast message may be controlled according the velocity of the user movement as well as the desired power control scheme.

Figure 6:
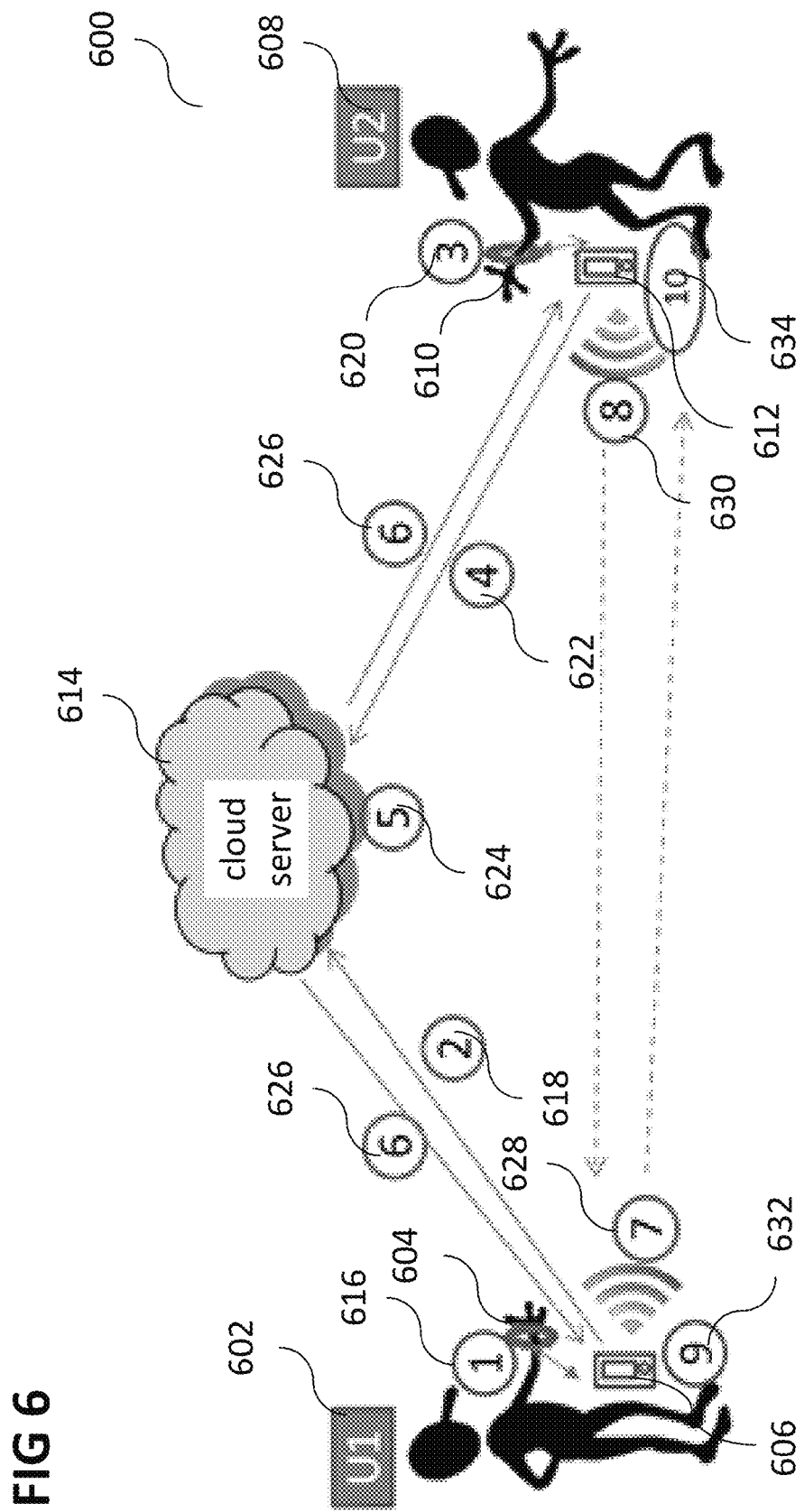

FIG. 6 shows an illustration 600 of an indirect information exchange and of a method for band to band information exchange according to various embodiments. A first user 602 (who may be referred to as U1) may have a first wearable device 604 (for example a first wristband) and a first mobile radio communication device 606 (for example a first mobile phone). A second user 608 (who may be referred to as U2) may have a second wearable device 610 (for example a second wristband) and a second mobile radio communication device 612 (for example a second mobile phone). A cloud server 614 may be provided.

In 616, the first user 602 (or his mobile radio communication device 606) may detect a connection between the first wearable device 604 and the first radio communication device 606 (for example a band connection to a phone). In 618, the first user 602 may update the location data (in other words: his geolocation) to the cloud server 614.

In 620, the second user 608 (or his mobile radio communication device 612) may detect a connection between the second wearable device 614 and the second radio communication device 612 (for example a band connection to a phone). In 622, the second user 622 may update the location data (in other words: his geolocation) to the cloud server 614.

In 624, the (cloud) server 614 may detect whether the first user 602 and the second user 608 are in the same vicinity based on the geolocation data. In 626, the (cloud) server 614 may inform the first user 602 and the second user 608 that there is another user in the vicinity (for example if it detects that the first user 602 and the second user 608 are in the same vicinity based on the geolocation data).

In 628, the first mobile radio communication device 606 may broadcast information of the first wearable device 604 (for example band information may be replicated in the mobile phone and then broadcasted). In 630, the second mobile radio communication device 612 may broadcast information of the second wearable device 610 (for example band information may be replicated in the mobile phone and then broadcasted).

In 632, the first user 602 (for example his mobile radio communication device 606) may receive information of the second wearable device 510 from the second mobile radio communication device 612 and may store the information in the first mobile radio communication device 606. In 634, the second user 608 (for example his mobile radio communication device 612) may receive information of the first wearable device 604 from the first mobile radio communication device 606 and may store the information in the second mobile radio communication device 612.

According to various embodiments, the mobile radio communication device, for example a mobile phone, may (for example via an app or application) constantly check for band connection and the phone may constantly update its location (geolocation) data to the server. The server may inform the phone to scan for surrounding bands when it detects more than one band in the same vicinity. Upon receiving command from server, each (mobile) phone may broadcast its band information (for example mimic the action of band). Each phone may also listen to broadcast info from the surrounding bands. Each phone may store the band information collected into its internal memory and subsequently upload the information to the server.

Power consumption of the band may be not affected with the implementation of this scheme. All the tasks may be carried out by the phone.

Figure 7:
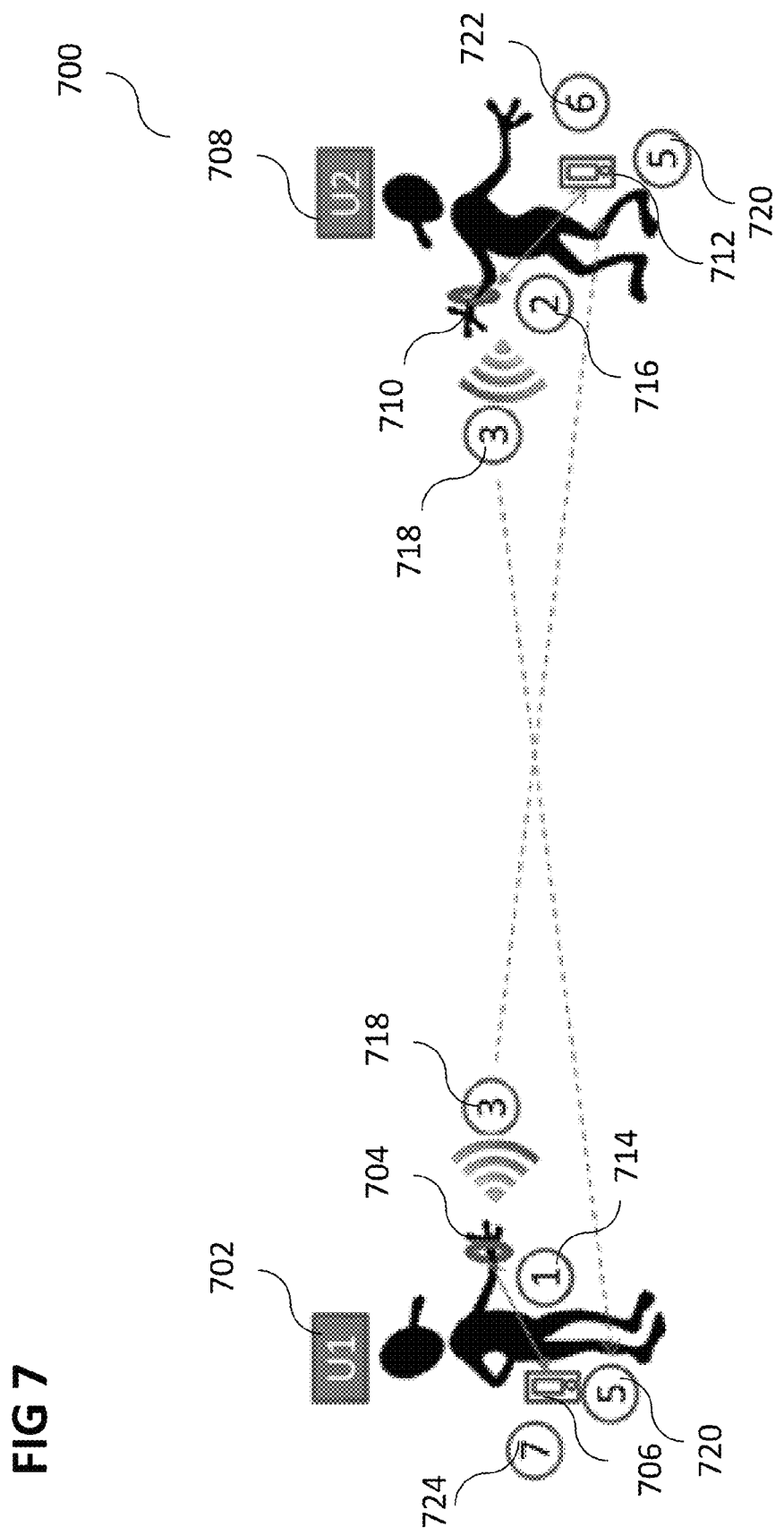

FIG. 7 shows an illustration 700 of an indirect information exchange and of a method for band to band information exchange according to various embodiments, which may be referred to as an offline mode. A first user 702 (who may be referred to as U1) may have a first wearable device 704 (for example a first wristband) and a first mobile radio communication device 706 (for example a first mobile phone). A second user 708 (who may be referred to as U2) may have a second wearable device 710 (for example a second wristband) and a second mobile radio communication device 712 (for example a second mobile phone).

In 714, the first user 702 (or his mobile radio communication device 706) may detect a connection between the first wearable device 704 and the first radio communication device 706 (for example a band connection to a phone). In 716, the second user 708 (or his mobile radio communication device 712) may detect a connection between the second wearable device 714 and the second radio communication device 712 (for example a band connection to a phone).

In 718, both the first user 702 and the second user 708 broadcast information via their respective wearable devices 704 and 710 at a set interval. The interval may be determined (or decided) by the mobile radio communication devices using geo location information set (in the mobile radio communication devices).

In 720, the mobile radio communication device 706 of the first user 702 and the mobile radio communication device 712 of the second user 708 may pick up broadcast information from the corresponding wearable devices (for example bands).

In 722, the first user 702 (for example his mobile radio communication device 706) may receive information from the second wearable device 710 and may store the information in the first mobile radio communication device 706. In 724, the second user 708 (for example his mobile radio communication device 712) may receive information from the first wearable device 704 and may store the information in the second mobile radio communication device 712.

When the respective mobile radio communication device (for example phone, for example mobile phone) is connected to a server, actual information may be retrieved via the server.

The method as described with reference to FIG. 7 may be tailored for a communication where there is no access server during the info exchange phase, and this method may be called offline mode. According to various embodiments, the band may act as a linked peripheral device for respective phone while at a set interval, broadcast band info so that neighboring users that within its signal range can pick up the broadcast packet.

The broadcast interval may be configured by the phone, for example when user is at home, it may make use of geo-location information to know broadcast and discovery may not be needed. The phone may then inform the band to de-activate or slow down the broadcast interval when user is at home.

Down side for such offline exchange may be a consumption of more energy than in the options described with reference to FIG. 5 and FIG. 6, but it may still be better than a conventional method of actual device to device communication.

According to various embodiments, wireless device to device information exchange may be provided where energy capacity is very limited by leveraging on higher capacity device to perform most of the task.

The wireless device to device communication according to various embodiments may provide wearable device which differentiate from others while maintaining the necessary energy capacity for other standard feature of a wearable devices.

According to various embodiments, devices and methods may be provided which leverage on the availability of wireless communication protocols such as BLE coupled with maturing handphone platform geo-location service.

The following examples pertain to further embodiments.

Example 1 is a radio communication system comprising: a portable device; a beacon receiving device; and a server; wherein the portable device comprises: a transmitter configured to repeatedly transmit signals; and a receiver configured to receive data from the server; wherein the beacon receiving device comprises: a receiver configured to receive signals from the portable device; and a transmitter configured to transmit an indication to the server based on the received signal; and wherein the server comprises: a receiver configured to receive the indication from the beacon receiving device; and a transmitter configured to transmit data to the portable device based on the indication.

In example 2, the subject-matter of example 1 can optionally include that the portable device is a mobile radio communication device.

In example 3, the subject-matter of any one of examples 1 to 2 can optionally include that the portable device comprises a mobile radio communication device and a wearable device.

In example 4, the subject-matter of example 3 can optionally include that the transmitter of the portable device is provided in the wearable device.

In example 5, the subject-matter of any one of examples 3 to 4 can optionally include that the receiver of the portable device is provided in the mobile radio communication device.

In example 6, the subject-matter of any one of examples 1 to 5 can optionally include that the indication comprises an identifier of the beacon receiving device.

In example 7, the subject-matter of any one of examples 1 to 6 can optionally include that the data comprises a coupon for a promotion at a location of the beacon receiving device.

In example 8, the subject-matter of any one of examples 1 to 7 can optionally include that the server further comprises a location tracking circuit configured to track a location of the portable device based on the indication.

In example 9, the subject-matter of example 8 can optionally include that the server further comprises a determination circuit configured to determine whether a further portable device moves jointly with the portable device based on the tracked location information.

In example 10, the subject-matter of example 9 can optionally include that the data comprises a coupon for a joint promotion for the user of the portable device and the user of the further portable device if the determination circuit determines that the further portable device moves jointly with the portable device.

In example 11, the subject-matter of any one of examples 9 to 10 can optionally include that the transmitter of the server is further configured to transmit the data to the further portable device if the determination circuit determines that the further portable device moves jointly with the portable device.

In example 12, the subject-matter of any one of examples 9 to 11 can optionally include that the beacon receiving device comprises a motion determination circuit configured to determine whether a motion of the portable device comprises a pre-determined motion.

In example 13, the subject-matter of example 12 can optionally include that the portable device comprises a motion determination circuit configured to determine whether a motion of the portable device comprises the pre-determined motion; wherein the transmitter of the portable device is further configured to transmit a motion identifier to the beacon receiving device if the motion determination circuit of the portable device determines that the motion of the portable device comprises the pre-determined motion; wherein the motion determination circuit of the beacon receiving device is configured to determine whether the motion of the portable device comprises the pre-determined motion based on the motion identifier; and wherein the indication comprises an identifier of the beacon receiving device, an identifier of the portable device and an identifier of the pre-determined motion if the motion determination circuit of the beacon receiving device determines that the motion of the portable device comprises the pre-determined motion.

In example 14, the subject-matter of example 13 can optionally include that the server comprises a determination circuit configured to determine whether at least two portable devices perform the pre-determined motion at the same location at the same time.

In example 15, the subject-matter of example 14 can optionally include that the server further comprises a social network circuit configured to link users of the at least two portable devices on a social network if the determination circuit of the server determines that at least two portable devices perform the pre-determined motion at the same location at the same time.

Example 16 is a radio communication method comprising: repeatedly transmitting signals from a portable device; receiving signals from the portable device in a beacon receiving device; transmitting an indication to the server from the beacon receiving device based on the received signal; receiving the indication from the beacon receiving device in a server; transmitting data from the server to the portable device based on the indication; and receiving data from the server in the portable device.

In example 17, the subject-matter of example 16 can optionally include that the portable device is a mobile radio communication device.

In example 18, the subject-matter of any one of examples 16 to 17 can optionally include that the portable device comprises a mobile radio communication device and a wearable device.

In example 19, the subject-matter of example 18 can optionally include that the repeatedly transmitting of signals from the portable device is performed by the wearable device.

In example 20, the subject-matter of any one of examples 18 to 19 can optionally include that the receiving of data from the server in the portable device is performed by the mobile radio communication device.

In example 21, the subject-matter of any one of examples 16 to 20 can optionally include that the indication comprises an identifier of the beacon receiving device.

In example 22, the subject-matter of any one of examples 16 to 21 can optionally include that the data comprises a coupon for a promotion at a location of the beacon receiving device.

In example 23, the subject-matter of any one of examples 16 to 22 can optionally include tracking in the server a location of the portable device based on the indication.

In example 24, the subject-matter of example 23 can optionally include: determining in the server whether a further portable device moves jointly with the portable device based on the tracked location information.

In example 25, the subject-matter of example 24 can optionally include that the data comprises a coupon for a joint promotion for the user of the portable device and the user of the further portable device if the server determines that the further portable device moves jointly with the portable device.

In example 26, the subject-matter of any one of examples 24 to 25 can optionally include: transmitting the data from the server to the further portable device if it is determined that the further portable device moves jointly with the portable device.

In example 27, the subject-matter of any one of examples 24 to 26 can optionally include: determining in the beacon receiving device whether a motion of the portable device comprises a pre-determined motion.

In example 28, the subject-matter of example 27 can optionally include: determining in the portable device whether a motion of the portable device comprises the pre-determined motion; transmitting a motion identifier from the portable device to the beacon receiving device if the portable device determines that the motion of the portable device comprises the pre-determined motion; wherein the beacon receiving device determines whether the motion of the portable device comprises the pre-determined motion based on the motion identifier; and wherein the indication comprises an identifier of the beacon receiving device, an identifier of the portable device and an identifier of the pre-determined motion if the beacon receiving device determines that the motion of the portable device comprises the pre-determined motion.

In example 29, the subject-matter of example 28 can optionally include: determining in the server whether at least two portable devices perform the pre-determined motion at the same location at the same time.

In example 30, the subject-matter of example 29 can optionally include: linking users of the at least two portable devices on a social network if the server determines that at least two portable devices perform the pre-determined motion at the same location at the same time.

Example 31 is a radio communication device, comprising: a memory circuit configured to store data to be broadcasted; a communication circuit configured to establish a wireless connection with a first further radio communication device; and a transmitter configured to at least one of broadcast signals based on the stored data or transmit a signal based on the stored data to the first further radio communication device using the communication circuit; wherein the communication circuit is configured to receive information from the first further radio communication device based on a signal broadcasted by a second further radio communication device, free from the communication circuit receiving the signal from the second further radio communication device.

In example 32, the subject-matter of example 31 can optionally include that the radio communication device is an ultra low power device.

In example 33, the subject-matter of any one of examples 31 to 32 can optionally include that the radio communication device is a wearable device.

In example 34, the subject-matter of any one of examples 31 to 33 can optionally include that the radio communication device is a wristband or is wearable to a body.

In example 35, the subject-matter of any one of examples 31 to 34 can optionally include that the transmitter is configured to broadcast signals according to a pre-determined timing scheme, the pre-determined timing scheme comprising a pre-determined number of transmission in a pre-determined period of time; the radio communication device further comprising: a device determination circuit configured to determine whether another radio communication device is in a communication range of the radio communication device; and a controller configured to change the pre-determined timing scheme to increase the number of transmissions in the pre-determined period of time if the device determination circuit determines that another radio communication device is in the communication range of the radio communication device.

In example 36, the subject-matter of example 35 can optionally include that the transmitter is configured to repeatedly transmit signals at a pre-determined time interval; and wherein the controller is configured to decrease the time interval if the device determination circuit determines that another radio communication device is in the communication range of the radio communication device.

In example 37, the subject-matter of any one of examples 35 to 36 can optionally include that the transmitter is configured to repeatedly transmit signals with a pre-determined frequency; and wherein the controller is configured to increase the frequency if the device determination circuit determines that another radio communication device is in the communication range of the radio communication device.

In example 38, the subject-matter of any one of examples 31 to 37 can optionally include that the transmitter is further configured to transmit information to another radio communication device in a communication session; the radio communication device further comprising: a device determination circuit configured to determine based on a location of the radio communication device whether another radio communication device is in a communication range of the radio communication device; and a controller configured to stop the communication session if the device determination circuit determines that no further radio communication device is in the communication range of the radio communication device.

In example 39, the subject-matter of any one of examples 31 to 38 can optionally include a motion determination circuit configured to determine whether a motion of the radio communication device comprises a pre-determined motion.

Example 40 is a radio communication system, comprising: the radio communication device of any one of examples 31 to 39; and the first further radio communication device.

In example 41, the subject-matter of example 40 can optionally include that the radio communication device is a wearable device; and wherein the first further radio communication device is a mobile phone.

In example 42, the subject-matter of example 41 can optionally include that the mobile phone is configured to transmit data indicating a location of the mobile phone to a server.

In example 43, the subject-matter of any one of examples 41 to 43 can optionally include that the mobile phone is configured to determine whether a further radio communication device is near the mobile phone.

In example 44, the subject-matter of example 43 can optionally include that the mobile phone is configured to determine whether a further radio communication device is near the mobile phone based on data received from a server.

In example 45, the subject-matter of any one of examples 43 to 44 can optionally include that the mobile phone is configured to instruct the wearable device to broadcast the signals based on the stored data if the mobile phone determines that a further radio communication device is near the mobile phone.

In example 46, the subject-matter of any one of examples 43 to 45 can optionally include that the wearable device is configured to transmit the signal based on the stored data to the mobile phone using the communication circuit; wherein the mobile phone is configured to broadcast the signals based on the signal transmitted from the wearable device if the mobile phone determines that a further radio communication device is near the mobile phone.

Example 47 is a method for controlling a radio communication device, the method comprising: storing data to be broadcasted; establishing a wireless connection with a first further radio communication device using a communication circuit; at least one of broadcasting signals based on the stored data or transmitting a signal based on the stored data to the first further radio communication device using the communication circuit; and receiving using the communication circuit information from the first further radio communication device based on a signal broadcasted by a second further radio communication device, free from the communication circuit receiving the signal from the second further radio communication device.

In example 48, the subject-matter of example 47 can optionally include that the radio communication device is an ultra low power device.

In example 49, the subject-matter of any one of examples 47 to 48 can optionally include that the radio communication device is a wearable device.

In example 50, the subject-matter of any one of examples 47 to 49 can optionally include that the radio communication device is a wristband or is wearable to a body.

In example 51, the subject-matter of any one of examples 47 to 50 can optionally include: broadcasting signals according to a pre-determined timing scheme, the pre-determined timing scheme comprising a pre-determined number of transmission in a pre-determined period of time; determining whether another radio communication device is in a communication range of the radio communication device; and changing the pre-determined timing scheme to increase the number of transmissions in the pre-determined period of time if the device determination circuit determines that another radio communication device is in the communication range of the radio communication device.

In example 52, the subject-matter of example 51 can optionally include: repeatedly transmitting signals at a pre-determined time interval; and decreasing the time interval if the device determination circuit determines that another radio communication device is in the communication range of the radio communication device.

In example 53, the subject-matter of any one of examples 51 to 52 can optionally include: repeatedly transmitting signals with a pre-determined frequency; and increasing the frequency if it is determined that another radio communication device is in the communication range of the radio communication device.

In example 54, the subject-matter of any one of examples 47 to 53 can optionally include: transmitting information to another radio communication device in a communication session; determining based on a location of the radio communication device whether another radio communication device is in a communication range of the radio communication device; and stopping the communication session if the device determination circuit determines that no further radio communication device is in the communication range of the radio communication device.

In example 55, the subject-matter of any one of examples 47 to 54 can optionally include: determining whether a motion of the radio communication device comprises a pre-determined motion.

Example 56 is a method for controlling a radio communication system, the method comprising: controlling a radio communication device according to the method of any one of examples 47 to 55; and controlling the first further radio communication device.

In example 57, the subject-matter of example 56 can optionally include that the radio communication device is a wearable device; and wherein the first further radio communication device is a mobile phone.

In example 58, the subject-matter of example 57 can optionally include: the mobile phone transmitting data indicating a location of the mobile phone to a server.

In example 59, the subject-matter of any one of examples 57 to 58 can optionally include: the mobile phone determining whether a further radio communication device is near the mobile phone.

In example 60, the subject-matter of example 59 can optionally include: the mobile phone determining whether a further radio communication device is near the mobile phone based on data received from a server.

In example 61, the subject-matter of any one of examples 59 to 60 can optionally include: the mobile phone instructing the wearable device to broadcast the signals based on the stored data if the mobile phone determines that a further radio communication device is near the mobile phone.

In example 62, the subject-matter of any one of examples 59 to 61 can optionally include: the wearable device transmitting the signal based on the stored data to the mobile phone using the communication circuit; and the mobile phone broadcasting the signals based on the signal transmitted from the wearable device if the mobile phone determines that a further radio communication device is near the mobile phone.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A radio communication system comprising:
a portable device;
and
a server;
wherein the portable device comprises:
a wearable device configured to repeatedly transmit signals to indicate presence of the wearable device to a beacon receiving device in vicinity of the wearable device; and
a radio communication device in short range communication with the wearable device;
wherein the server comprises:
a receiver configured to receive an indication from the beacon receiving device, the indication indicative of the presence of the wearable device;
a transmitter configured to transmit data to the radio communication device upon receiving the indication; and
a determination circuit configured to detect a further wearable device in vicinity of the wearable device;
wherein upon detection of the further wearable device, the transmitter is further configured to instruct the radio communication device and a further radio communication device in short range communication with the further wearable device, to respectively control the wearable device and the further wearable device to broadcast information.

2. The radio communication system of claim 1, wherein the wearable device comprises a portable device transmitter.

3. The radio communication system of claim 1, wherein the radio communication device comprises a portable device receiver.

4. The radio communication system of claim 1, wherein the indication comprises an identifier of the beacon receiving device.

5. The radio communication system of claim 1, wherein the data comprises a coupon for a promotion at a location of the beacon receiving device.

6. The radio communication system of claim 1, wherein the data comprises a coupon for a joint promotion for the user of the portable device and the user of the further portable device if the determination circuit determines that the further portable device moves jointly with the portable device.

7. The radio communication system of claim 1, wherein the beacon receiving device comprises a motion determination circuit configured to determine whether a motion of the portable device comprises a pre-determined motion.

8. The radio communication system of claim 7, wherein the portable device comprises a motion determination circuit configured to determine whether a motion of the portable device comprises the pre-determined motion;
wherein a transmitter of the portable device is further configured to transmit a motion identifier to the beacon receiving device if the motion determination circuit of the portable device determines that the motion of the portable device comprises the pre-determined motion;
wherein the motion determination circuit of the beacon receiving device is configured to determine whether the motion of the portable device comprises the pre-determined motion based on the motion identifier; and
wherein the indication comprises an identifier of the beacon receiving device, an identifier of the portable device and an identifier of the pre-determined motion if the motion determination circuit of the beacon receiving device determines that the motion of the portable device comprises the pre-determined motion.

9. The radio communication system of claim 8, wherein the determination circuit is further configured to determine whether at least two portable devices perform the pre-determined motion at the same location at the same time.

10. The radio communication system of claim 9, wherein the server further comprises a social network circuit configured to link users of the at least two portable devices on a social network if the determination circuit of the server determines that at least two portable devices perform the pre-determined motion at the same location at the same time.

11. A radio communication method comprising:
indicating presence of a wearable device of a portable device by repeatedly transmitting signals from the wearable device to a beacon receiving device;
receiving an indication from the beacon receiving device in a server, the indication indicative of the presence of the wearable device;
upon receiving the indication, transmitting data from the server to a radio communication device of the portable device, the radio communication device being in short range communication with the wearable device;
detecting a further wearable device in vicinity of the wearable device, using a determination circuit of the server; and
upon detection of the further wearable device, instructing the radio communication device and a further radio communication device in short range communication with the further wearable device, to respectively control the wearable device and the further wearable device to broadcast information.

12. The radio communication method of claim 11, wherein the indication comprises an identifier of the beacon receiving device.

13. The radio communication method of claim 11, wherein the data comprises a coupon for a promotion at a location of the beacon receiving device.

14. The radio communication method of claim 11, wherein the data comprises a coupon for a joint promotion for the user of the portable device and the user of the further portable device if the server determines that the further portable device moves jointly with the portable device.

15. The radio communication method of claim 11, further comprising:
determining in the beacon receiving device whether a motion of the portable device comprises a pre-determined motion.

16. The radio communication method of claim 15, further comprising:
determining in the portable device whether the motion of the portable device comprises the pre-determined motion;
transmitting a motion identifier from the portable device to the beacon receiving device if the portable device determines that the motion of the portable device comprises the pre-determined motion;
wherein the beacon receiving device determines whether the motion of the portable device comprises the pre-determined motion based on the motion identifier; and
wherein the indication comprises an identifier of the beacon receiving device, an identifier of the portable device and an identifier of the pre-determined motion if the beacon receiving device determines that the motion of the portable device comprises the pre-determined motion.

17. The radio communication method of claim 16, further comprising:
determining in the server whether at least two portable devices perform the pre-determined motion at the same location at the same time.

18. A server comprising:
a receiver configured to receive an indication from a beacon receiving device, the indication indicative of a presence of a wearable device;
a transmitter configured to transmit data to a radio communication device in short range communication with the wearable device upon receiving the indication; and
a determination circuit configured to detect a further wearable device in vicinity of the wearable device;
wherein upon detection of the further wearable device, the transmitter is further configured to instruct the radio communication device and a further radio communication device in short range communication with the further wearable device, to respectively control the wearable device and the further wearable device to broadcast information.

* * * * *